US012650423B2

(12) United States Patent
Peled et al.

(10) Patent No.: US 12,650,423 B2
(45) Date of Patent: Jun. 9, 2026

(54) PHARMACEUTICAL COMPOSITIONS AND USE THEREOF

(71) Applicant: HADASIT MEDICAL RESEARCH SERVICES & DEVELOPMENT LTD., Jerusalem (IL)

(72) Inventors: Amnon Peled, Tel Aviv (IL); Shira Levi, Jerusalem (IL)

(73) Assignee: HADASIT MEDICAL RESEARCH SERVICES & DEVELOPMENT LTD., Jerusalem (IL)

( * ) Notice: Subject to any disclaimer, the term of this patent is extended or adjusted under 35 U.S.C. 154(b) by 831 days.

(21) Appl. No.: 17/912,951

(22) PCT Filed: Mar. 22, 2021

(86) PCT No.: PCT/IL2021/050318
§ 371 (c)(1),
(2) Date: Sep. 20, 2022

(87) PCT Pub. No.: WO2021/191895
PCT Pub. Date: Sep. 30, 2021

(65) Prior Publication Data
US 2023/0133409 A1 May 4, 2023

Related U.S. Application Data

(60) Provisional application No. 62/993,011, filed on Mar. 22, 2020.

(51) Int. Cl.
| | |
|---|---|
| *C07H 21/04* | (2006.01) |
| *A61K 31/05* | (2006.01) |
| *A61K 31/14* | (2006.01) |
| *A61K 31/343* | (2006.01) |
| *A61K 31/40* | (2006.01) |
| *A61K 31/4196* | (2006.01) |
| *A61K 31/4439* | (2006.01) |
| *A61K 31/445* | (2006.01) |
| *A61K 31/498* | (2006.01) |
| *A61K 31/519* | (2006.01) |
| *A61K 38/13* | (2006.01) |
| *A61P 35/00* | (2006.01) |
| *C07K 16/28* | (2006.01) |
| *G01N 33/50* | (2006.01) |

(52) U.S. Cl.
CPC ......... *G01N 33/5023* (2013.01); *A61K 31/05* (2013.01); *A61K 31/14* (2013.01); *A61K 31/343* (2013.01); *A61K 31/40* (2013.01); *A61K 31/4196* (2013.01); *A61K 31/4439* (2013.01); *A61K 31/445* (2013.01); *A61K*

*31/498* (2013.01); *A61K 31/519* (2013.01); *A61K 38/13* (2013.01); *A61P 35/00* (2018.01); *C07K 16/2827* (2013.01); *G01N 33/5044* (2013.01)

(58) Field of Classification Search
CPC ....................................................... A61P 37/00
See application file for complete search history.

(56) References Cited

U.S. PATENT DOCUMENTS

2002/0159974 A1    10/2002    Mach

OTHER PUBLICATIONS

Yun et al. (Blood Advances, 2019, 3, 16, 2448-2452).*
Alexander et al. (Oncotarget, 2017, 8, 9, 14897-14911).*
Palliyage et al. (Lung Cancer 181 (2023) 107258, 1-14).*
Hirashima et al. (Anticancer Research 39: 6231-6240 (2019)).*
Chan D, Binks S, Nicholas JM, Frost C, Cardoso MJ, Ourselin S, Wilkie D, Nicholas R, Chataway J. Effect of high-dose simvastatin on cognitive, neuropsychiatric, and health-related quality-of-life measures in secondary progressive multiple sclerosis: secondary analyses from the MS-STAT randomised, placebo-controlled trial. Lancet Neurol. Aug. 2017;16(8):591-600. doi: 10.1016/S1474-4422(17)30113-8. Epub Jun. 7, 2017. PMID: 28600189; PMCID: PMC5507768.
Mercier J, Voutsadakis IA. A Systematic Review and Meta-analysis of Retrospective Series of Regorafenib for Treatment of Metastatic Colorectal Cancer. Anticancer Res. Nov. 2017;37(11):5925-5934. doi: 10.21873/anticanres.12039. PMID: 29061771.
Micewicz ED, Khachatoorian R, French SW, Ruchala P. Identification of novel small-molecule inhibitors of Zika virus infection. Bioorg Med Chem Lett. Feb. 1, 2018;28(3):452-458. doi: 10.1016/j.bmcl.2017.12.019. Epub Dec. 9, 2017. PMID: 29258771.
Ock CY, Kim S, Keam B, Kim S, Ahn YO, Chung EJ, Kim JH, Kim TM, Kwon SK, Jeon YK, Jung KC, Kim DW, Wu HG, Sung MW, Heo DS. Changes in programmed death-ligand 1 expression during cisplatin treatment in patients with head and neck squamous cell carcinoma. Oncotarget. Jun. 16, 2017;8(58):97920-97927. doi: 10.18632/oncotarget.18542.PMID: 29228662; PMCID: PMC5716702.
Tuan NM, Lee CH. Penfluridol as a Candidate of Drug Repurposing for Anticancer Agent. Molecules. Oct. 11, 2019;24(20):3659. doi: 10.3390/molecules24203659. PMID: 31614431; PMCID: PMC6832311.

(Continued)

*Primary Examiner* — Amy Rose Hudson
(74) *Attorney, Agent, or Firm* — The Roy Gross Law Firm, LLC; Roy D. Gross

(57) ABSTRACT

The present invention is directed to a method for treating an IFN-γ associated disease or disorder in a subject in need thereof, including administering to the subject a pharmaceutical composition including a therapeutically effective amount of a compound capable of manipulating or modulating PD-L1 signaling or pathway.

6 Claims, 15 Drawing Sheets

Specification includes a Sequence Listing.

(56)                    References Cited

OTHER PUBLICATIONS

Dunn GP, Sheehan KC, Old LJ, Schreiber RD. IFN unresponsiveness in LNCaP cells due to the lack of JAK1 gene expression. Cancer Res. Apr. 15, 2005;65(8):3447-53. doi: 10.1158/0008-5472. CAN-04-4316. PMID: 15833880.

Kang S, Brown HM, Hwang S. Direct Antiviral Mechanisms of Interferon-Gamma. Immune Netw. Oct. 17, 2018;18(5):e33. doi: 10.4110/in.2018.18.e33. PMID: 30402328; PMCID: PMC6215902.

Garcia-Diaz A, Shin DS, Moreno BH, Saco J, Escuin-Ordinas H, Rodriguez GA, Zaretsky JM, Sun L, Hugo W, Wang X, Parisi G, Saus CP, Torrejon DY, Graeber TG, Comin-Anduix B, Hu-Lieskovan S, Damoiseaux R, Lo RS, Ribas A. Interferon Receptor Signaling Pathways Regulating PD-L1 and PD-L2 Expression. Cell Rep. May 9, 2017;19(6):1189-1201. doi: 10.1016/j.celrep.2017.04. 031. Erratum in: Cell Rep. Dec. 10, 2019;29(11):3766. PMID: 28494868; PMCID: PMC6420824.

Haanen Jbag. Converting Cold into Hot Tumors by Combining Immunotherapies. Cell. Sep. 7, 2017;170(6):1055-1056. doi: 10.1016/j.cell.2017.08.031. PMID: 28886376.

Wald O, Weiss ID, Wald H, Shoham H, Bar-Shavit Y, Beider K, Galun E, Weiss L, Flaishon L, Shachar I, Nagler A, Lu B, Gerard C, Gao JL, Mishani E, Farber J, Peled A. IFN-gamma acts on T cells to induce NK cell mobilization and accumulation in target organs. J Immunol. Apr. 15, 2006;176(8):4716-29. doi: 10.4049/jimmunol. 176.8.4716. PMID: 16585565.

Weiss ID, Wald O, Wald H, Beider K, Abraham M, Galun E, Nagler A, Peled A. IFN-gamma treatment at early stages of influenza virus infection protects mice from death in a NK cell-dependent manner. J Interferon Cytokine Res. Jun. 2010;30(6):439-49. doi: 10.1089/jir.2009.0084. PMID: 20235626.

Peled, A. (Nov. 2020). Targeting Novel Immune Response Pathways [Slide show; Presentation].

T F Gajewski, F W Fitch; Anti-proliferative effect of IFN-gamma in immune regulation. I. IFN-gamma inhibits the proliferation of Th2 but not Th1 murine helper T lymphocyte clones. J Immunol Jun. 15, 1988; 140 (12): 4245-4252. https://doi.org/10.4049/jimmunol.140. 12.4245.

PCT International Search Report for International Application No. PCT/IL2021/050318, mailed Jul. 18, 2021, 4pp.

PCT Written Opinion for International Application No. PCT/IL2021/050318, mailed Jul. 18, 2021, 7pp.

PCT International Preliminary Report on Patentability for International Application No. PCT/IL2021/050318, issued Sep. 22, 2022, 8pp.

Cattaneo Dario et al., "Therapeutic use of HMG-COA reductase inhibitors: current practice and future perspectives", Expert Opinion on Therapeutic Patents, Taylor and Francis, GB, vol. 14, No. 11, Jan. 1, 2004.

Roskoski, Robert Jr., et al., "Janus Kinase (JAK) inhibitors in the treatment of inflammatory and neoplastic diseases" Pharmacological Research, Elsevier, Amsterdam NL, vol. 111, pp. 784-803, Jul. 26, 2016.

* cited by examiner

SEQUENCE LISTING

```
<160> NUMBER OF SEQ ID NOS: 1

<210> SEQ ID NO 1
<211> LENGTH: 9599
<212> TYPE: DNA
<213> ORGANISM: Artificial Sequence
<220> FEATURE:
<223> OTHER INFORMATION: Synthetic

<400> SEQUENCE: 1
agccaccatg gtgagcaagg gcgaggagct gttcaccggg gtggtgccca tcctggtcga      60
gctggacggc gacgtaaacg gccacaagtt cagcgtgtcc ggcgagggcg agggcgatgc     120
cacctacggc aagctgaccc tgaagttcat ctgcaccacc ggcaagctgc ccgtgccctg     180
gcccaccctc gtgaccaccc tgacctacgg cgtgcagtgc ttcagccgct accccgacca     240
catgaagcag cacgacttct tcaagtccgc catgcccgaa ggctacgtcc aggagcgcac     300
catcttcttc aaggacgacg gcaactacaa gacccgcgcc gaggtgaagt tcgagggcga     360
caccctggtg aaccgcatcg agctgaaggg catcgacttc aaggaggacg gcaacatcct     420
ggggcacaag ctggagtaca actacaacag ccacaacgtc tatatcatgg ccgacaagca     480
gaagaacggc atcaaggtga acttcaagat ccgccacaac atcgaggacg gcagcgtgca     540
gctcgccgac cactaccagc agaacacccc catcggcgac ggccccgtgc tgctgcccga     600
caaccactac ctgagcaccc agtccgccct gagcaaagac cccaacgaga agcgcgatca     660
catggtcctg ctggagttcg tgaccgccgc cgggatcact ctcggcatgg acgagctgta     720
caagtagctc gagctgtgga atgtgtgtca gttagggtgt ggaaagtccc caggctcccc     780
agcaggcaga agtatgcaaa gcatgcatct caattagtca gcaaccaggt gtggaaagtc     840
cccaggctcc ccagcaggca gaagtatgca aagcatgcat ctcaattagt cagcaaccat     900
agtcccgccc ctaactccgc ccatcccgcc cctaactccg cccagttccg cccattctcc     960
gccccatggc tgactaattt tttttattta tgcagaggcc gaggccgcct ctgcctctga    1020
gctattccag aagtagtgag gaggcttttt tggaggccta ggcttttgca aaaagctccc    1080
gggagcttgt atatccattt tcggatctga tcggcgcggg ccgcgatccc gcccctctcc    1140 ctccccccc cctaacgtta ctggccgaag ccgcttggaa taaggccggt gtgcgtttgt    1200
ctatatgtta ttttccacca tattgccgtc ttttggcaat gtgagggccc ggaaacctgg    1260
```

```
ccctgtcttc ttgacgagca ttcctagggg tctttcccct ctcgccaaag gaatgcaagg      1320
tctgttgaat gtcgtgaagg aagcagttcc tctggaagct tcttgaagac aaacaacgtc      1380
tgtagcgacc ctttgcaggc agcggaaccc cccacctggc gacaggtgcc tctgcggcca      1440
aaagccacgt gtataagata cacctgcaaa ggcggcacaa ccccagtgcc acgttgtgag      1500
ttggatagtt gtggaaagag tcaaatggct ctcctcaagc gtattcaaca aggggctgaa      1560
ggatgcccag aaggtacccc attgtatggg atctgatctg gggcctcggt gcacatgctt      1620
tacatgtgtt tagtcgaggt taaaaaaacg tctaggcccc ccgaaccacg gggacgtggt      1680
tttcctttga aaaacacgat gataagcttg ccacaaccca caaggagacg accttccatg      1740
accgagtaca agcccacggt gcgcctcgcc acccgcgacg acgtcccccg ggccgtacgc      1800
accctcgccg ccgcgttcgc cgactacccc gccacgcgcc acaccgtcga cccggaccgc      1860
cacatcgagc gggtcaccga gctgcaagaa ctcttcctca cgcgcgtcgg gctcgacatc      1920
ggcaaggtgt gggtcgcgga cgacggcgcc gcggtggcgg tctggaccac gccggagagc      1980
gtcgaagcgg gggcggtgtt cgccgagatc ggcccgcgca tggccgagtt gagcggttcc      2040
cggctggccg cgcagcaaca gatggaaggc ctcctggcgc cgcaccggcc caaggagccc      2100
gcgtggttcc tggccaccgt cggcgtctcg cccgaccacc agggcaaggg tctgggcagc      2160
gccgtcgtgc tccccggagt ggaggcggcc gagcgcgccg gggtgcccgc cttcctggag      2220
acctccgcgc ccgcaacct ccccttctac gagcggctcg gcttcaccgt caccgccgac      2280
gtcgaggtgc ccgaaggacc gcgcacctgg tgcatgaccc gcaagcccgg tgcctagacg      2340
cgtctggaac aatcaacctc tggattacaa aatttgtgaa agattgactg gtattcttaa      2400
ctatgttgct cctttacgc tatgtggata cgctgcttta atgcctttgt atcatgctat      2460
tgcttcccgt atggctttca ttttctcctc cttgtataaa tcctggttgc tgtctcttta      2520
tgaggagttg tggcccgttg tcaggcaacg tggcgtggtg tgcactgtgt ttgctgacgc      2580 aaccccact ggttggggca ttgccaccac ctgtcagctc ctttccggga cttcgctt      2640 cccctccct attgccacgg cggaactcat cgccgcctgc cttgcccgct gctggacagg      2700
ggctcggctg ttgggcactg acaattccgt ggtgttgtcg gggaagctga cgtcctttcc      2760
atggctgctc gcctgtgttg ccacctggat tctgcgcggg acgtccttct gctacgtccc      2820
ttcggccctc aatccagcgg accttccttc ccgcggcctg ctgccggctc tgcggcctct      2880
tccgcgtctt cgccttcgcc ctcagacgag tcggatctcc ctttgggccg cctccccgcc      2940
tggaattaat tctgcagtcg agacctagaa aaacatggag caatcacaag tagcaataca      3000
gcagctacca atgctgattg tgcctggcta gaagcacaag aggaggagga ggtgggtttt      3060
tccagtcaca cctcaggacc tttaagacca atgacttaca aggcagctgt agatcttagc      3120 cacttttttaa aagaaaagag gggactggaa gggctaattc actcccaacg aagacaagat      3180
ctgctttttg cctgtactgg gtctctctgg ttagaccaga tctgagcctg ggagctctct      3240
ggctaactag ggaacccact gcttaagcct caataaagct tgccttgagt gcttcaagta      3300
gtgtgtgccc gtctgttgtg tgactctggt aactagagat ccctcagacc cttttagtca      3360
gtgtggaaaa tctctagcag tagtagttca tgtcatctta ttattcagta tttataactt      3420
gcaaagaaat gaatatcaga gagtgagagg ctagcgtttt accgtcgacc tctagctaga      3480
gcttggcgta atcatggtca tagctgtttc ctgtgtgaaa ttgttatccg ctcacaattc      3540
cacacaacat acgagccgga agcataaagt gtaaagcctg gggtgcctaa tgagtgagct      3600
```

```
aactcacatt aattgcgttg cgctcactgc ccgctttcca gtcgggaaac ctgtcgtgcc    3660
agctgcatta atgaatcggc caacgcgcgg ggagaggcgg tttgcgtatt gggcgctctt    3720
ccgcttcctc gctcactgac tcgctgcgct cggtcgttcg gctgcggcga gcggtatcag    3780
ctcactcaaa ggcggtaata cggttatcca cagaatcagg ggataacgca ggaaagaaca    3840
tgtgagcaaa aggccagcaa aaggccagga accgtaaaaa ggccgcgttg ctggcgtttt    3900
tccataggct ccgcccccct gacgagcatc acaaaaatcg acgctcaagt cagaggtggc    3960
gaaacccgac aggactataa agataccagg cgtttccccc tggaagctcc ctcgtgcgct    4020
ctcctgttcc gaccctgccg cttaccggat acctgtccgc ctttctccct tcgggaagcg    4080
tggcgctttc tcatagctca cgctgtaggt atctcagttc ggtgtaggtc gttcgctcca    4140
agctgggctg tgtgcacgaa ccccccgttc agcccgaccg ctgcgcctta ccggtaact    4200 atcgtcttga gtccaacccg gtaagacacg acttatcgcc actggcagca gccactggta    4260
acaggattag cagagcgagg tatgtaggcg gtgctacaga gttcttgaag tggtggccta    4320
actacggcta cactagaaga acagtatttg gtatctgcgc tctgctgaag ccagttacct    4380
tcggaaaaag agttggtagc tcttgatccg gcaaacaaac caccgctggt agcggttttt    4440
ttgtttgcaa gcagcagatt acgcgcagaa aaaaaggatc tcaagaagat cctttgatct    4500
tttctacggg gtctgacgct cagtggaacg aaaactcacg ttaagggatt ttggtcatga    4560
gattatcaaa aaggatcttc acctagatcc ttttaaatta aaaatgaagt tttaaatcaa    4620
tctaaagtat atatgagtaa acttggtctg acagttacca atgcttaatc agtgaggcac    4680
ctatctcagc gatctgtcta tttcgttcat ccatagttgc ctgactcccc gtcgtgtaga    4740
taactacgat acgggagggc ttaccatctg gccccagtgc tgcaatgata ccgcgagacc    4800
cacgctcacc ggctccagat ttatcagcaa taaaccagcc agccggaagg gccgagcgca    4860
gaagtggtcc tgcaacttta tccgcctcca tccagtctat taattgttgc cgggaagcta    4920
gagtaagtag ttcgccagtt aatagtttgc gcaacgttgt tgccattgct acaggcatcg    4980
tggtgtcacg ctcgtcgttt ggtatggctt cattcagctc cggttcccaa cgatcaaggc    5040
gagttacatg atccccatg ttgtgcaaaa aagcggttag ctccttcggt cctccgatcg    5100
ttgtcagaag taagttggcc gcagtgttat cactcatggt tatggcagca ctgcataatt    5160
ctcttactgt catgccatcc gtaagatgct tttctgtgac tggtgagtac tcaaccaagt    5220
cattctgaga atagtgtatg cggcgaccga gttgctcttg cccggcgtca atacgggata    5280
ataccgcgcc acatagcaga actttaaaag tgctcatcat tggaaaacgt tcttcggggc    5340
gaaaactctc aaggatctta ccgctgttga tccagttc gatgtaaccc actcgtgcac    5400
ccaactgatc ttcagcatct tttactttca ccagcgtttc tgggtgagca aaaacaggaa    5460
ggcaaaatgc cgcaaaaaag ggaataaggg cgacacggaa atgttgaata ctcatactct    5520
tcctttttca atattattga agcatttatc agggttattg tctcatgagc ggatacatat    5580
ttgaatgtat ttagaaaaat aaacaaatag gggttccgcg cacatttccc cgaaaagtgc    5640
cacctgacgt cgacggatcg ggagatcaac ttgtttattg cagcttataa tggttacaaa    5700
taaagcaata gcatcacaaa tttcacaaat aaagcatttt tttcactgca ttctagttgt    5760
ggtttgtcca aactcatcaa tgtatcttat catgtctgga tcaactggat aactcaagct    5820
aaccaaaatc atcccaaact tcccacccca taccctatta ccactgccaa ttaccctgtg    5880
ggcgcaatta accctcacta aagggaacaa aagctggagc tgcaagctta atgtagtctt    5940
atgcaatact cttgtagtct tgcaacatgg taacgatgag ttagcaacat gccttacaag    6000
```

```
gagagaaaaa gcaccgtgca tgccgattgg tggaagtaag gtggtacgat cgtgccttat    6060
taggaaggca acagacgggt ctgacatgga ttggacgaac cactgaattg ccgcattgca    6120
gagatattgt atttaagtgc ctagctcgat acataaacgg gtctctctgg ttagaccaga    6180
tctgagcctg ggagctctct ggctaactag ggaacccact gcttaagcct caataaagct    6240
tgccttgagt gcttcaagta gtgtgtgccc gtctgttgtg tgactctggt aactagagat    6300
ccctcagacc cttttagtca gtgtggaaaa tctctagcag tggcgcccga acagggactt    6360
gaaagcgaaa gggaaaccag aggagctctc tcgacgcagg actcggcttg ctgaagcgcg    6420
cacggcaaga ggcgaggggc ggcgactggt gagtacgcca aaaattttga ctagcggagg    6480
ctagaaggag agagatgggt gcgagagcgt cagtattaag cggggagaa ttagatcgcg    6540 atgggaaaaa attcggttaa ggccaggggg aagaaaaaa tataaattaa aacatatagt    6600
atgggcaagc agggagctag aacgattcgc agttaatcct ggcctgttag aaacatcaga    6660
aggctgtaga caaatactgg gacagctaca accatccctt cagacaggat cagaagaact    6720
tagatcatta tataatacag tagcaaccct ctattgtgtg catcaaagga tagagataaa    6780
agacaccaag gaagctttag acaagataga ggaagagcaa aacaaaagta agaccaccgc    6840
acagcaagcg gccggccgct gatcttcaga cctggaggag gagatatgag ggacaattaa    6900
ttggagaagt gaattatata aatataaagt agtaaaaatt gaaccattag gagtagcacc    6960
caccaaggca aagagaagag tggtgcagag agaaaaaaga gcagtgggaa taggagcttt    7020
gttccttggg ttcttgggag cagcaggaag cactatgggc gcagcgtcaa tgacgctgac    7080
ggtacaggcc agacaattat tgtctggtat agtgcagcag cagaacaatt tgctgagggc    7140
tattgaggcg caacagcatc tgttgcaact cacagtctgg ggcatcaagc agctccaggc    7200
aagaatcctg gctgtggaaa gatacctaaa ggatcaacag ctcctgggga tttggggttg    7260
ctctggaaaa ctcatttgca ccactgctgt gccttggaat gctagttgga gtaataaatc    7320
tctggaacag atttggaatc acacgacctg gatggagtgg gacagagaaa ttaacaatta    7380
cacaagctta atacactcct taattgaaga atcgcaaaac cagcaagaaa agaatgaaca    7440
agaattattg gaattagata aatgggcaag tttgtggaat tggtttaaca taacaaattg    7500
gctgtggtat ataaaattat tcataatgat agtaggaggc ttggtaggtt taagaatagt    7560
ttttgctgta ctttctatag tgaatagagt taggcaggga tattcaccat tatcgtttca    7620
gacccacctc ccaaccccga ggggacccga caggcccgaa ggaatagaag aagaaggtgg    7680
agagagagac agagacagat ccattcgatt agtgaacgga tctcgacggt atcgccttta    7740
aaagaaaagg ggggattggg gggtacagtg cagggggaag aatagtagac ataatagcaa    7800
cagacataca aactaaagaa ctacaaaaac aaattacaaa aattcaaaat tttcgggttt    7860
attacaggga cagcagagat ccagtttatc taatacgact cactataggg agagagagag    7920
aattaccctc actaaaggga ggagaagcat gaattgaagg agatagaacc agatcttgga    7980
attcactaag ccagcggaca ccccagtatt cacccagtgc actactttgg aatagtagtt    8040
ttgtaagtaa gtggggggaaa gcagagaatg aagaaggccc ttgaagtcca acagtgaaat    8100
gtttaaagat gacagtgctc tgtggagttc ccaaggtttt gtcttggaaa aagtccacac    8160
ttccagttcg cagaaagtct ttctcaacat catttagaat agacttcccc cacctggatc    8220
ccgagactgg ccgtgatcca cagcgttcac aaagggcacg gttcgagatg ggaagttctt    8280
gaacggcaag acaactggtt tcattatgtc gaggaacttt gaggaagtca ccaaatccac    8340
```

-continued

```
gatttaaaaa tatatttcct attatacaga cacacctact ttctagaatt aaaactgagt    8400
catttgcttg atattaactc tataggttgt ataactctat atgtaaagtc atgtcaagac    8460
tgtcacgtat ccacgtatcc agaaagggct tgaaagagat ggggaatcgg atggtaattt    8520
gaagtgtctg gattctgaag ataaaattta agtcagagat cttatgactt cagatatttt    8580
gcttctaaag cgctcactgc tcaagcctga agatttgaaa ttcgggtcct cattacccat    8640
aataaatgca gtgatggccc atttctgaga ccctagccct ggcagcaggg gcgcggatgg    8700
ggatccctgg accacgctgg ccggctagtt tggccagctg cgagcccgag gttaggtaag    8760
agagaccctc tttcaaaaat caaggtggga gctgtagagg aaggcaacct atgtggatct    8820
ccaagcacac gctcccccec accccacce ccgacctcag gttccactcc cacccaaaat    8880
agagctgagt tgtttactct ggactgtttc tttgagggaa cctgatttac aagaaagcta    8940
atgcaggttt cactttcact tttagtttcg tttttaaata gtgtttgttt gtttttgttt    9000
ttatcgacag cctctcagta gcagcccggt tgtcttggag ctctctctat agaccagaga    9060
ctcacctgcc actggctcct gagtactgga attaaggcgt gtgtcaccgc accgaagcct    9120
agtttcgttt tttcttaaac tgtgaatatc ccaaagctga ctctaaagtc atccgcagga    9180
aatactatga gataaactca tgctcaaagg gactgggtgg cttcggtttc acagacagcg    9240
gaggttggac aaggcttccg cggagtgggc ggggctctga actcgagata agaccaggaa    9300
atcgtggtcc ccaagcctca tgccaggctg cacttgcacg tcgcgggcca gtctcctcgc    9360
ctgcaggtaa gggagcatct tctcgcggaa tccgcttgca gggcacttta aagagccaga    9420
atccctagac ctttttagga cggagaaggg aaccggtttc ctgggaaagt taagaactca    9480
gaatccgcag ttttgtgtgt ttatggatct tgtgggtagg tagctgggtc agaagagatg    9540
aattaattgg tcctagcgcg acttgactgt ttgctaagct tggtaccgag ctcggatcc     9599
```

PHARMACEUTICAL COMPOSITIONS AND USE THEREOF

CROSS-REFERENCE TO RELATED APPLICATIONS

This application is a National Phase of PCT Patent Application No. PCT/IL2021/050318 having International filing date of Mar. 22, 2021, which claims the benefit of priority to U.S. Provisional Patent Application No. 62/993, 011, titled: "PHARMACEUTICAL COMPOSITIONS AND USE THEREOF", filed Mar. 22, 2020, the contents of which are all incorporated herein by reference in their entirety.

FIELD OF THE INVENTION

The present invention is directed to pharmaceutical compositions and methods of using same, such as for treating autoimmune disease, inflammation, viral infection, and cancer.

BACKGROUND

Interferon γ (IFN-γ) is a pleiotropic cytokine produced mainly by natural killer (NK) cells and specific T-cell subsets and monocytes that plays a central role in promoting innate and adaptive mechanisms of host defense by immune regulation. The biological actions of IFN-γ are particularly broad because almost all normal cells express functionally active IFN-γ receptors on their surface. IFN-γ activates natural and specific immunity against virus infected cells and cancer cells.

IFNγ is a key cytokine in the polarization and recruitment of Th1 (CD8+ T cells). IFNγ upregulates the chemokines CXCL9 and CXCL10 that attract cytotoxic cells into tumors and viral infected tissues. In parallel to promoting innate and adaptive mechanisms of host defense, IFNγ negatively regulates the magnitude of immune response by upregulating the immune checkpoint cell surface receptor PD-L1.

In humans, blocking PD-L1 or its ligand PD-1 increases anti-tumor effects of T cells and at the other extreme induces autoimmune disease. In humans, tumors that express IFNγ, CXCL10, and PD-L1 have a better chance to response to anti PD-1/PD-L1 therapy and are considered hot tumors.

Administration of IFN-γ was shown to stimulate the mobilization of NK cells and their accumulation in the peritoneum, liver, and tumor bearing lung tissue. Furthermore, increased numbers of NK cells in the lung reduced metastasis of Lewis lung carcinoma cells resulting in significantly extended NK-dependent survival.

Sequential administration of IFN-γ at an early stage of an infection was demonstrated to protect infected mice from death in a NK cell-dependent manner. Interestingly, there was no significant faster clearance of the virus following IFN-γ treatment. However, IFN-γ treatment significantly reduced recruitment of immune cells to the lung at the inflammatory phase following infection. Thus, reducing inflammation by shaping cellular and cytokine profiles may favorably change the fate of viral pathogenesis.

SUMMARY

The present invention in some embodiments, is directed to a method for treating an IFN-γ associated disease or disorder in a subject in need thereof, including administering to the subject a pharmaceutical composition including a therapeutically effective amount of a compound capable of manipulating or modulating PD-L1 signaling or pathway.

The present invention, in some embodiments, is based, in part, on the finding that an immunosensor can determine the interferon gamma (IFN-γ) dependent status and over-express it in LPA cells that respond to IFN-γ by upregulation of PDL-1 and CXCL10. As disclosed herein below, a sensor containing a reporter gene, e.g., the green fluorescence protein (GFP), that is linked to the mouse PDL-1 promoter can be used in the kits and methods of the invention (see, FIG. 14).

According to a first aspect, there is provided a method for treating an IFN-γ associated disease or disorder in a subject in need thereof, the method comprising administering to the subject a pharmaceutical composition comprising a therapeutically effective amount of: (i) a compound selected from the group consisting of the compounds listed in Table 3, wherein the disease is selected from a viral infection, GVHD, inflammation and autoimmunity; (ii) a compound selected from the group consisting of the compounds listed in Table 2, wherein the disease is selected from a viral infection, GVHD, and cancer; (iii) a compound selected from the group consisting of the compounds listed in Table 1, wherein the disease is selected from autoimmunity, inflammation, and viral infection; and (iv) a compound selected from the group consisting of the compounds listed in Table 4, wherein the disease is cancer; thereby treating an IFN-γ associated disease or disorder in the subject.

According to another aspect there is provided, a method for identifying the suitability of a compound for treatment of an IFN-γ associated disease or disorder, the method comprising: contacting a cell with the compound and determining the expression levels of PD-L1 and CXCL10, wherein upregulation of PD-L1 and significant downregulation of CXCL10 indicates that the compound is effective in treating a disease or disorder selected from autoimmunity, inflammation, and viral infection; wherein upregulation of PD-L1 and upregulation, having no effect on or mild downregulation of CXCL10 expression indicates that the compound is effective in treating a disease or disorder selected from viral infection, GVHD, and cancer; wherein downregulation of both PD-L1 and CXCL10 indicates that the compound is effective in treating a disease or disorder selected from viral infection, GVHD, inflammation and autoimmunity; and wherein downregulation of PD-L1 and upregulation, having no effect on or mild downregulation of CXCL10 is indicative that the compound is effective in treating cancer.

In some embodiments, the compound of Table 1 upregulates PD-L1 and significantly down regulates CXCL10 in the subject.

In some embodiments, the compound of Table 2 upregulates PD-L1 and increases, has no effect on, or mildly reduces CXCL10 expression in the subject.

In some embodiments, the compound of Table 3 downregulates both PD-L1 and CXCL10 in the subject.

In some embodiments, the compound of Table 4 downregulates PD-L1 and upregulates, has no effect on or mildly down regulates CXCL10 in the subject.

In some embodiments, the disease is cancer, and the method further comprises administering an anti-PD-L1 therapy to the subject.

In some embodiments, the anti-PD-L1 therapy is administered concomitantly to or after the administering a pharmaceutical composition.

In some embodiments, determining the expression levels of PD-L1 is performed using an immunosensor comprising a PD-L1 promotor operably linked to a reporter gene.

In some embodiments, determining the expression levels of CXCL10 is by an immunoassay.

In some embodiments, the immunoassay is enzyme-linked immunosorbent assay (ELISA).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In addition to the exemplary aspects and embodiments described above, further aspects and embodiments will become apparent by reference to the figures and by study of the following detailed description.

BRIEF DESCRIPTION OF THE FIGURES

FIGS. 15B-15C include histological micrographs of the mouse DTH model. (15B) a control mouse. (15C) a mouse treated with Deferasirox. (15D) a mouse treated with Penfluridol. (15E) includes a vertical graph showing the effect of selected compounds (Ganetespib, Dinaciclib, Penfluridol, and Deferasirox) on the ear thickness in the mouse DTH model. Dexamethasone, a known anti-inflammatory agent was used a positive control.

DETAILED DESCRIPTION

Figure 1A:
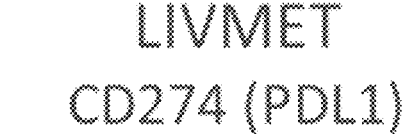
FIGS. 1A-1B include vertical bar graphs showing the expression levels of PD-L1 (1A) and CXCL10 (1B) in LivMet cells in the absence (UT) or presence of interferon γ (IFN-γ).
Figure 1A:
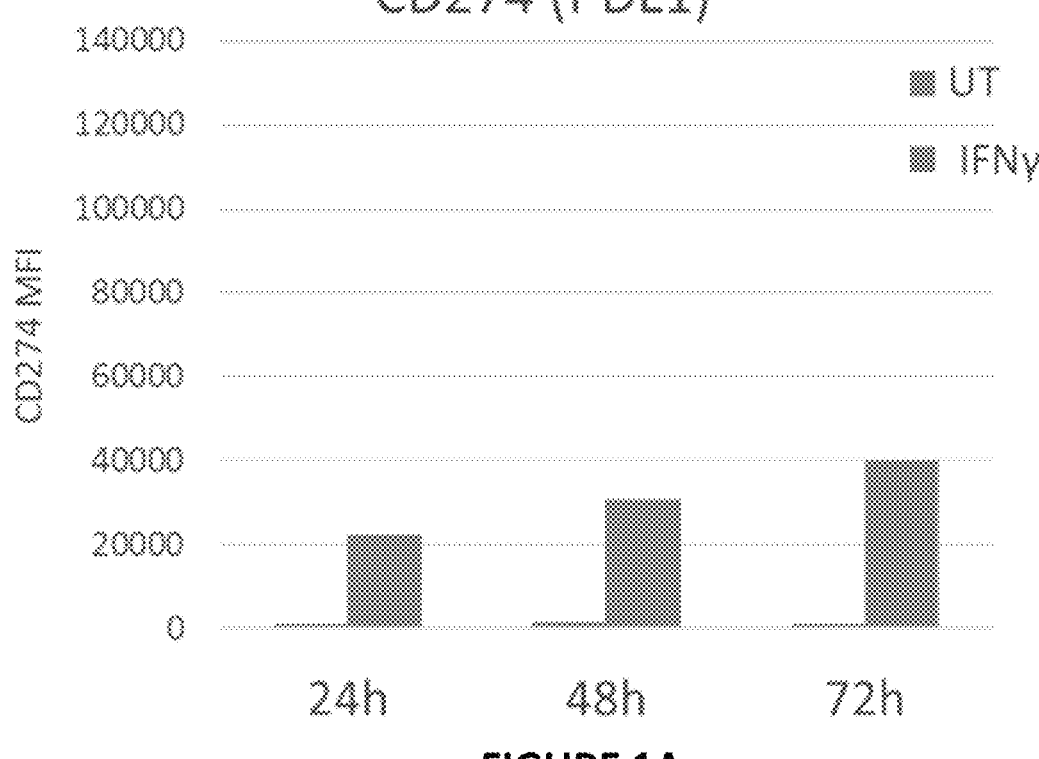

The present invention, in some embodiments thereof, is directed to a method for manipulating or modulating INF-γ-mediated response, in a subject in need thereof.

The invention further provides methods for identifying the suitability of a compound for treatment of an IFN-γ associated disease or disorder, comprising contacting a cell with the compound and determining the expression levels of PD-L1 and CXCL10.

The invention further provides methods, composition and kits, for identifying the suitability of a compound for treatment of an IFN-γ associated disease or disorder.

The present invention, in some embodiments thereof, is directed to a method for manipulating or modulating INF-γ-mediated PD-L1 response. In some embodiments, INF-γ-mediated response is INF-γ-mediated PD-L1 response. In some embodiments, modulating is increasing or decreasing. In some embodiments, manipulating or modulating the INF-γ-mediated PD-L1 response comprises the manipulation or modulation of PD-L1, CXCL10, or any combination thereof.

In some embodiments, the method further comprises manipulating or modulating CXCL9.

As used herein, the term "PD-L1 response" comprises numerous cellular components associated with PD-L1 signaling or pathway. In some embodiments, the method comprises manipulating or modulating PD-L1 signaling or pathway.

Cellular components involved or related to PD-L1 signaling or pathway, would be apparent to one of ordinary skill in the art of molecular and cellular biology.

In some embodiments manipulating or modulating is achieved by contacting a subject in need thereof or a cell thereof with a therapeutically effective amount of a compound capable of upregulating PD-L1, downregulating PD-L1, upregulating, having no effect on or mildly down-regulating CXCL10, down regulating, having no effect on or mildly upregulating CXCL10, downregulating CXCL10, or any combination thereof. In some embodiments, upregulating, having no effect on or mildly downregulating is not significantly downregulating.

As used herein, the term "significantly", e.g., significantly upregulate, significantly downregulate, etc., is by at least 50% more, at least 60% more, at least 70% more, at least 80% more, at least 90% more, at least 95% more, or at least 99% more, or any value and range therebetween. Each possibility represents a separate embodiment of the invention. In some embodiments, significantly is by 50-60% more, 50-70% more, 50-80% more, 50-90% more, 50-100% more, 60-70% more, 60-80% more, 50-90% more, 60-100% more, 70-80% more, 70-80% more, 70-90% more, 70-100% more, 80-90% more, 80-100% more, 90-95% more, 90-99% more, or 90-100% more. Each possibility represents a separate embodiment of the invention.

As used herein, the term "mildly", e.g., mildly upregulate, mildly downregulate, etc., is by 10% at most, 20% at most, 30% at most, 40% at most, or 50% at most, or any value and range therebetween. Each possibility represents a separate embodiment of the invention. In some embodiments, mildly is by 20-30%, 20-40%, 20-50%, 30-40%, 30-50%, or 40-50%. Each possibility represents a separate embodiment of the invention. In some embodiments, mildly, e.g., mildly upregulate, mildly downregulate, etc. is by less than 50%.

In some embodiments, the present method is directed to treating or preventing an autoimmune disease or condition, inflammation, or viral infection in a subject in need thereof.

In some embodiments, the present method is directed to treating or preventing graft versus host disease (GVHD), or cancer progression (e.g., from stage 1 to stage 2, from stage 3 to stage 4, from local tumor to metathesis, etc.). In some embodiments, the method is directed to treating or preventing GVHD, cancer or viral infection.

In some embodiments, the present method is direct to treating or preventing viral infection, GVHD, autoimmune disease or condition, or inflammation.

In some embodiments, the present method is directed to treating or preventing cancer.

As used herein, the term "cancer" encompasses a cell proliferation related disease.

According to some embodiments, there is provided a method for treating an IFN-γ associated disease or disorder in a subject in need thereof, comprising administering to the subject a pharmaceutical composition comprising a therapeutically effective amount of: (i) a compound selected from the group consisting of the compounds listed in Table 1, wherein the disease is selected from autoimmunity, inflammation, and viral infection; (ii) a compound selected from the group consisting of the compounds listed in Table 2, wherein the disease is selected from a viral infection, GVHD, and cancer; (iii) a compound selected from the group consisting of the compounds listed in Table 3, wherein the disease is selected from a viral infection, GVHD, inflammation and autoimmunity; and (iv) a compound selected from the group consisting of the compounds listed in Table 4, wherein the disease is cancer; thereby treating an IFN-γ associated disease or disorder in the subject.

In some embodiments, the pharmaceutical composition comprises a compound selected from the group of compounds listed in Table 1 and wherein the disease is selected from autoimmunity, inflammation, and viral infection. In some embodiments, the pharmaceutical composition comprises a compound selected from the group of compounds listed in Table 2 and wherein the disease is selected from viral infection, GVHD and cancer. In some embodiments, the pharmaceutical composition comprises a compound selected from the group of compounds listed in Table 3 and wherein the disease is selected from autoimmunity, inflammation, GVHD and viral infection. In some embodiments, the pharmaceutical composition comprises a compound selected from the group of compounds listed in Table 4 and wherein the disease is cancer. In some embodiments, there is provided a compound for use in the upregulation of PD-L1 and downregulation of CXCL10. In some embodiments, downregulation is significant downregulation. In some embodiment the compound upregulating PD-L1 and significantly down regulating CXCL10 is selected from Table 1.

TABLE 1

A list of compounds that upregulate PD-L1
and significantly down regulate CXCL10.

| Compound | CAS Number | Biosimilar compounds (generics, derivatives, etc.) |
|---|---|---|
| Deferasirox | 201530-41-8 | Exjade, Desirox, Defrijet, Desifer, Rasiroxpine and Jadenu |
| Clofazimine | 2030-63-9 | Lamprene |
| Dronedarone HCl | 141625-93-6 | Class III antiarrhythmic drugs amiodarone |
| Axitinib (AG 013736) | 319460-85-0 | |
| Benzethonium Chloride | 121-54-0 | Methylbenzethonium chloride |
| Cetylpyridinium Chloride | 123-03-5 | Cationic quaternary ammonium |
| Terfenadine | 50679-08-8 | Antihistamine |
| Cyclosporin A | 59865-13-3 | |
| Glycopyrrolate | 596-51-0 | Muscarinic anticholinergic |
| Chlorocresol | 59-50-7 | |
| Docetaxel Trihydrate | 148408-66-6 | |
| Epirubicin HCl | 56390-09-1 | |
| Doxorubicin (Adriamycin) HCl | 25316-40-9 | |
| S- (+)-Rolipram | 85416-73-5 | Phosphodiesterase-4 inhibitors |

In some embodiments, any biosimilar compound (e.g., generics, derivatives, etc.) listed in any one of Tables 1-4, can be used according to the herein disclosed method as a substitute for its corresponding compound listed in the tables (in the "Compound column").

In some embodiments, Deferasirox can be used for treating or preventing a disease or a condition selected from: autoimmunity, inflammatory, viral infection, or a combination thereof.

In some embodiments, Clofazimine can be used for treating or preventing a disease or a condition selected from: autoimmunity, viral infection, or a combination thereof.

In some embodiments, Dronedarone HCl can be used for treating or preventing a disease or a condition selected from: autoimmunity, inflammatory, viral infection, or a combination thereof.

In some embodiments, Axitinib can be used for treating or preventing a disease or a condition selected from: autoimmunity, inflammatory, viral infection, or a combination thereof.

In some embodiments, Benzethonium Chloride can be used for treating or preventing a disease or a condition selected from: autoimmunity, inflammatory, or a combination thereof.

In some embodiments, Cetylpyridinium Chloride can be used for treating or preventing a disease or a condition selected from: autoimmunity, inflammatory, or a combination thereof.

In some embodiments, Terfenadine can be used for treating or preventing a disease or a condition selected from: autoimmunity, inflammatory, viral infection, or a combination thereof.

In some embodiments, Cyclosporin A can be used for treating or preventing a viral infection, or a combination thereof.

In some embodiments, Glycopyrrolate can be used for treating or preventing a disease or a condition selected from: autoimmunity, inflammatory, viral infection, or a combination thereof.

In some embodiments, Chlorocresol can be used for treating or preventing a disease or a condition selected from: autoimmunity, inflammatory, viral infection, or a combination thereof.

In some embodiments, Docetaxel trihydrate can be used for treating or preventing a disease or a condition selected from: autoimmunity, inflammatory, viral infection, or a combination thereof.

In some embodiments, Epirubicin Hydrochloride can be used for treating or preventing a disease or a condition selected from: autoimmunity, inflammatory, viral infection, or a combination thereof.

In some embodiments, Doxorubicin Hydrochloride can be used for treating or preventing a disease or a condition selected from: autoimmunity, inflammatory, viral infection, or a combination thereof.

In some embodiments, S-(+)-Rolipram (is the (S)-enantiomer of rolipram) can be used for treating or preventing a disease or a condition selected from: autoimmunity, inflammatory, viral infection, or a combination thereof.

In some embodiments, there is provided a compound for use in the upregulation of PD-L1 and increase or mild reduction of CXCL10. In some embodiments, there is provided a compound for use in the upregulation of PD-L1 and increase, not effecting or mild reduction of CXCL10. In some embodiments, there is provided a compound for use in the upregulation of PD-L1 and not significant downregulation of CXCL10. In some embodiment the compound upregulating PD-L1 and increasing, not effecting or mildly reducing of CXCL10 is selected from Table 2.

TABLE 2

A list of compounds that upregulate PD-L1 and increase or mildly reduce CXCL10 expression.

| Compound | CAS Number | Biosimilar compounds (generics, derivatives, etc.) |
|---|---|---|
| Penfluridol | 26864-56-2 | |
| Pizotifen | 15574-96-6 | |
| Mechlorethamine HCl | 55-86-7 | |
| Trifluridine (Viroptic) | 70-00-8 | Anti-herpesvirus antiviral drug |
| Cytarabine hydrochloride | 69-74-9 | |
| Sunitinib | 557795-19-4 | |
| Plerixafor 8HCl | 155148-31-5 | |
| FT-207 (NSC 148958) | 17902-23-7 | |
| Raltitrexed | 112887-68-0 | |

TABLE 2-continued

A list of compounds that upregulate PD-L1 and increase or mildly reduce CXCL10 expression.

| Compound | CAS Number | Biosimilar compounds (generics, derivatives, etc.) |
|---|---|---|
| Carbimazole | 22232-54-8 | |
| Mycophenolic acid | 483-60-3 | |
| Cinepazide maleate | 26328-04-1 | Tradename Vasodistal Brindel |
| Azathioprine | 446-86-6 | Imuran |
| Esmolol HCl | 81161-17-3 | Betal receptor blockers |
| Cabozantinib malate | 1140909-48-3 | Cabometyx and Cometriq |
| Sucralose | 56038-13-2 | |
| Nefiracetam | 77191-36-7 | |
| Drospirenone | 67392-87-4 | |
| Zaltoprofen | 74711-43-6 | Selective COX-2 inhibitors |
| Procarbazine HCl | 366-70-1 | |
| Otilonium Bromide | 0026095-59-0 | |
| Idarubicin HCl | 57852-57-0 | |
| Etoposide | 33419-42-0 | |
| IPI-145 (INK1197) | 1201438-56-3 | Duvelisib, sold under the brand name Copiktra, |
| Mercaptopurine (6-MP) | 50-44-2 | |
| Irinotecan | 97682-44-5 | |
| Cabozantinib | 849217-68-1 | |
| Carmofur | 61422-45-5 | |
| Empagliflozin (BI 10773) | 864070-44-0 | |
| Clarithromycin | 81103-11-9 | Macrolide antibiotics |
| Rasagiline Mesylate | 161735-79-1 | |
| Sunitinib malate | 341031-54-7 | |
| Trilostane | 13647-35-3 | |
| Amonafide | 69408-81-7 | |

In some embodiments, Penfluridol can be used for treating or preventing a disease or a condition selected from: viral infection, GVHD, cancer, or a combination thereof.

In some embodiments, Pizotifen can be used for treating or preventing a disease or a condition selected from: viral infection, GVHD, cancer, or a combination thereof.

In some embodiments, mechlorethamine hydrochloride can be used for treating or preventing a disease or a condition selected from: viral infection, GVHD, cancer, or a combination thereof. In some embodiments, cancer is cancer progression.

In some embodiments, Trifluridine (Viroptic) can be used for treating or preventing a disease or a condition selected from: viral infection, GVHD, cancer, or a combination thereof.

In some embodiments, Cytarabine Hydrochloride can be used for treating or preventing a disease or a condition selected from: viral infection, GVHD, cancer, or a combination thereof.

In some embodiments, Sunitinib can be used for treating or preventing a disease or a condition selected from: viral infection, GVHD, or a combination thereof.

In some embodiments, Plerixafor can be used for treating or preventing a disease or a condition selected from: viral infection, GVHD, cancer, or a combination thereof.

In some embodiments, Tegafur (e.g., FT-207 (NSC 148958) can be used for treating or preventing a disease or a condition selected from: viral infection, GVHD, or a combination thereof.

In some embodiments, Raltitrexed can be used for treating or preventing a disease or a condition selected from: viral infection, GVHD, or a combination thereof.

In some embodiments, Carbimazole can be used for treating or preventing a disease or a condition selected from: viral infection, GVHD, cancer, or a combination thereof.

In some embodiments, Mycophenolic acid can be used for treating or preventing a disease or a condition selected from: viral infection, cancer, or a combination thereof.

In some embodiments, Cinepazide maleate can be used for treating or preventing a disease or a condition selected from: viral infection, GVHD, cancer, or a combination thereof.

In some embodiments, Azathioprine can be used for treating or preventing a disease or a condition selected from: viral infection, cancer, or a combination thereof.

In some embodiments, Esmolol Hydrochloride can be used for treating or preventing a disease or a condition selected from: viral infection, GVHD, cancer, or a combination thereof.

In some embodiments, Cabozantinib malate can be used for treating or preventing a disease or a condition selected from: viral infection, GVHD, or a combination thereof.

In some embodiments, Sucralose can be used for treating or preventing a disease or a condition selected from: viral infection, GVHD, cancer, or a combination thereof.

In some embodiments, Nefiracetam can be used for treating or preventing a disease or a condition selected from: viral infection, GVHD, cancer, or a combination thereof.

In some embodiments, Drospirenone can be used for treating or preventing a disease or a condition selected from: viral infection, GVHD, cancer, or a combination thereof.

In some embodiments, Zaltoprofen can be used for treating or preventing a disease or a condition selected from: viral infection, GVHD, cancer, or a combination thereof.

In some embodiments, Procarbazine Hydrochloride can be used for treating or preventing a disease or a condition selected from: viral infection, GVHD, or a combination thereof.

In some embodiments, Otilinium Bromide can be used for treating or preventing a disease or a condition selected from: viral infection, GVHD, cancer, or a combination thereof.

In some embodiments, Idarubicin Hydrochloride can be used for treating or preventing a disease or a condition selected from: viral infection, GVHD, cancer, or a combination thereof.

In some embodiments, Etoposide can be used for treating or preventing a disease or a condition selected from: viral infection, GVHD, or a combination thereof.

In some embodiments, Duvelisib (e.g., IPI-145 (INK1197) can be used for treating or preventing a disease or a condition selected from: viral infection, GVHD, or a combination thereof.

In some embodiments, Mercaptopurine can be used for treating or preventing a disease or a condition selected from: viral infection, GVHD, or a combination thereof.

In some embodiments, Irinotecan can be used for treating or preventing a disease or a condition selected from: viral infection, GVHD, or a combination thereof.

In some embodiments, Cabozantinib can be used for treating or preventing a disease or a condition selected from: viral infection, GVHD, or a combination thereof.

In some embodiments, Carmofur can be used for treating or preventing a disease or a condition selected from: viral infection, GVHD, or a combination thereof.

In some embodiments, Empagliflozin can be used for treating or preventing a disease or a condition selected from: viral infection, GVHD, cancer, or a combination thereof.

In some embodiments, Clarithromycin can be used for treating or preventing a disease or a condition selected from: viral infection, GVHD, cancer, or a combination thereof.

In some embodiments, Rasagiline mesylate can be used for treating or preventing a disease or a condition selected from: viral infection, GVHD, cancer, or a combination thereof.

In some embodiments, Sunitinib malate can be used for treating or preventing a disease or a condition selected from: viral infection, GVHD, or a combination thereof.

In some embodiments, Trilostane can be used for treating or preventing a disease or a condition selected from: viral infection, GVHD, cancer, or a combination thereof.

In some embodiments, Amonafide can be used for treating or preventing a disease or a condition selected from: viral infection, GVHD, or a combination thereof.

In some embodiments, the method of treating cancer further comprises a step of administering an anti-PD-L1 based therapy to the subject. In some embodiments, the method of treating cancer further comprises a step of administering an anti-PD-L1 therapy to the subject. In some embodiments, the pharmaceutical composition further comprises an anti-PD-L1 therapy. In some embodiments, the molecules for treating cancer are for use in combination with an anti-PD-L1 therapy.

In some embodiments, the anti-PD-L1 therapy is PD-L1 blockade. In some embodiments, that anti-PD-L1 therapy is an anti-PD-L1 antibody. Anti-PD-L1 antibodies are well known in the art and include but are not limited to cemiplimab, nivolumab, pembrolizumab, avelumab, durvalumab and atezolizumab. In some embodiments, the anti-PD-L1 therapy is administered concomitantly with the pharmaceutical composition. In some embodiments, the anti-PD-L1 therapy is administered after the administration of the pharmaceutical composition. In some embodiments, after is after a time sufficient for the upregulation of PD-L1 expression in the subject.

In some embodiments, there is provided a compound for use in the downregulation of both PD-L1 and CXCL10. In some embodiment the compound downregulating both PD-L1 and CXCL10 is selected from Table 3.

TABLE 3

| A list of drugs that down regulate PD-L1 and down regulate CXCL10. | | |
| --- | --- | --- |
| Compound | CAS Number | Biosimilar compounds (generics, derivatives, etc.) |
| Dinaciclib | 779353-01-4 | |
| Ganetespib | 888216-25-9 | |
| Ruxolitinib | 941678-49-5 | Jakafi and Jakavi |
| Baricitinib | 1187594-09-7 | Olumiant |
| Mevastatin | 73573-88-3 | Compactin, ML-236B |
| AZD-9291 | 1421373-65-0 | Osimertinib (previously known as mereletinib; trade name Tagrisso) |
| BI6727 | 755038-65-4 | Volasertib |
| Simvastatin | 79902-63-9 | |
| Heparin sodium | 9041-08-1 | |
| Pitavastatin Calcium | 147511-69-1 | |
| Pelitinib (EKB-569) | 257933-82-7 | |
| Ponatinib (AP24534) | 943319-70-8 | |
| Mevastatin | 73573-88-3 | Compactin, ML-236B |
| AZD-9291 | 1421373-65-0 | Osimertinib (previously known as mereletinib; trade name Tagrisso) |

In some embodiments, Dinaciclib can be used for treating or preventing a disease or a condition selected from: viral infection, GVHD, inflammation, autoimmunity, or a combination thereof. Dinaciclib showed a significant anti-inflammatory effect in-vitro and in-vivo and therefor has the higher potential to treat or prevent an autoimmune disease or condition, inflammation, or viral infection.

According to some embodiments, there is provided a pharmaceutical composition comprising Dinaciclib, for use in the treatment or prevention of a disease or a disorder selected from: viral infection, GVHD, inflammation, autoimmunity, or any combination thereof.

In some embodiments, Ganetespib can be used for treating or preventing a disease or a condition selected from: viral infection, GVHD, inflammation, autoimmunity, or a combination thereof.

In some embodiments, Ruxolitinib can be used for treating or preventing a disease or a condition selected from: viral infection, GVHD, autoimmunity, or a combination thereof.

In some embodiments, Mevastatin can be used for treating or preventing a disease or a condition selected from: viral infection, GVHD, inflammation, autoimmunity, or a combination thereof.

In some embodiments, Baricitinib can be used for treating or preventing a disease or a condition selected from: viral infection, GVHD, inflammation, autoimmunity, or a combination thereof.

In some embodiments, AZD-9291 can be used for treating or preventing a disease or a condition selected from: viral infection, GVHD, inflammation, autoimmunity, or a combination thereof.

In some embodiments, BI6727 (e.g., Volasertib) can be used for treating or preventing a disease or a condition selected from: viral infection, GVHD, inflammation, autoimmunity, or a combination thereof.

In some embodiments, Simvastatin can be used for treating or preventing a disease or a condition selected from: viral infection, inflammation, autoimmunity, or a combination thereof.

In some embodiments, Heparin Sodium can be used for treating or preventing a disease or a condition selected from: viral infection, GVHD, inflammation, autoimmunity, or a combination thereof.

In some embodiments, Pitavastatin calcium can be used for treating or preventing a disease or a condition selected from: viral infection, GVHD, inflammation, autoimmunity, or a combination thereof.

In some embodiments, Pelitinib (e.g., EKB-569) can be used for treating or preventing a disease or a condition selected from: viral infection, GVHD, inflammation, autoimmunity, or a combination thereof.

In some embodiments, Ponatinib can be used for treating or preventing a disease or a condition selected from: viral infection, GVHD, inflammation, autoimmunity, or a combination thereof.

In some embodiments, there is provided a compound for use in the downregulation of PD-L1 and upregulation or mild downregulation of CXCL10. In some embodiments, there is provided a compound for use in the downregulation of PD-L1 and upregulation, not effecting or mild downregulation of CXCL10. In some embodiment the compound downregulating PD-L1 and upregulating, not effecting of mildly downregulating CXCL10 is selected from Table 4.

12

TABLE 4

| A list of compounds that downregulate PD-L1 and upregulate or mildly downregulate CXCL10. | | |
| --- | --- | --- |
| Compound | CAS Number | Biosimilar compounds (generics, derivatives, etc.) |
| Avanafil | 330784-47-9 | Stendra |
| Chlorhexidine HCl | 3697-42-5 | |
| Regorafenib | 755037-03-7 | Stivarga |

In some embodiments, Avanafil can be used for treating or preventing cancer.

In some embodiments, Chlorhexidine HCl can be used for treating or preventing cancer.

In some embodiments, Regorafenib can be used for treating or preventing cancer.

Screening Assays

In some embodiments, there is provided a method for identifying the suitability of a compound for treatment of an IFN-γ associated disease or disorder, comprising: contacting a cell with the compound and determining the expression levels of PD-L1 and CXCL10.

In some embodiments, upregulation of PD-L1 and significant downregulation of CXCL10 is indicative of the compound being effective in treating a disease or disorder selected from: autoimmunity, inflammation, and viral infection.

In some embodiments, upregulation of PD-L1 and upregulation or mild downregulation of CXCL10 expression is indicative of the compound being effective in treating a disease or disorder selected from: viral infection, GVHD, and cancer.

In some embodiments, downregulation of both PD-L1 and CXCL10 is indicative of the compound being effective in treating a disease or disorder selected from viral infection, GVHD, inflammation and autoimmunity.

In some embodiments, downregulation of PD-L1 and upregulation or mild downregulation of CXCL10 is indicative of the compound being effective in treating cancer.

In some embodiments, determining the expression levels of PD-L1 is performed using an immunosensor as disclosed herein. In some embodiments, the immunosensor comprises a PD-L1 promotor. In some embodiments, the promoter is operably linked to a reporter gene.

In some embodiments, determining the expression levels of CXCL10 is by an immunoassay. In some embodiments, the immunoassay is ELISA.

Methods utilizing antibodies for various detection and quantification (e.g., immunoassays) are common and would be apparent to one of ordinary skill in the art of biochemistry and cell biology. A non-limiting example for such immunoassay includes, but is not limited to ELISA, e.g., direct or indirect ELISA.

In some embodiments, the cell is a murine cell. In some embodiments, the cell is a mouse cell. In some embodiments, the cell is a human cell. In some embodiments, the cell is a mammalian cell. In some embodiments, the cell is a cancer cell. In some embodiments, the cell is not a cancer cell. In some embodiments, the cell is a primary cell. In some embodiments, the cell is a cell of a cell line.

Methods of Determining Suitability of a Subject for Therapy (e.g., Transplantation)

In some embodiments, there is provided a method for determining the suitability of a subject for therapy. In some embodiments, the therapy is a transplantation. In some embodiments, transplantation is an organ transplantation. In some embodiments the method comprises obtaining or providing a sample from the subject. In some embodiments, the method comprises the step of contacting the herein disclosed immunosensor with a sample of the subject and determining the expression levels of the reporter gene. In some embodiments, the method comprises a step of determining the level of expression of the reporter gene in the presence of the subject's sample compared to the level of expression of the reporter gene in the absence of the subject's sample. In some embodiments, the method further comprises a step of determining the expression level of CXCL10 in the immunosensor in the presence and in the absence of the subject's sample. In some embodiments, reduction in the expression levels of both the reporter gene and CXCL10 in the presence of the subject's sample (compared to control, e.g., in the absence of the subject's sample) is indicative of the subject is not suitable for a therapy, e.g., a transplantation. In some embodiments, upregulation in the expression levels of the reporter gene and upregulation or a mild reduction in the expression level of CXCL10 in the presence of the subject's sample (compared to control, e.g., in the absence of the subject's sample) is indicative of the subject is not suitable for a therapy, e.g., a transplantation.

In some embodiments, the method further comprises a step of manipulating or modulating the expression levels of PD-L1, CXCL10, or both in a subject determined as being not suitable for therapy, e.g., a transplantation, using a compound as disclosed herein.

In some embodiments, the sample is derived or obtained from the subject. In some embodiments, the sample comprises any cell type, tissue, organ, bodily fluid, or any combination thereof of the subject.

In some embodiments, the determination step as disclosed herein is performed in vitro.

According to some embodiments, there is provided a method for treating or preventing a disease or a disorder selected from the group: viral infection, GVHD, inflammation, autoimmunity, and any combination thereof, in a subject in need thereof, the method comprising administering to said subject a pharmaceutical composition comprising a therapeutically effective amount of Dinaciclib, thereby treating or preventing a disease or a disorder selected from the group: viral infection, GVHD, inflammation, autoimmunity, and any combination thereof, in the subject.

In some embodiments, the administering comprises a single administering or multiple administering.

In some embodiments, the administering comprises intravenously administering.

According to some embodiments, there is provided an expression vector or a plasmid comprising a PD-L1 promoter, and an exogenous reporter gene operably linked thereto.

In some embodiments, the expression vector or plasmid comprises any reporter gene configured to be expressed under the regulation of a PD-L1 promoter.

In some embodiments, the reporter gene is a bioluminescent reporter gene. In some embodiments, the reporter gene is a chemiluminescent reporter gene. In some embodiments, the reporter gene is a fluorescent reporter gene.

Types of reporter genes, including their sequence, and optimal conditions for reaction, are common and would be apparent to one of ordinary skill in the art. In some embodiments, the reporter gene is a green fluorescence protein (GFP). In one embodiment, GFP comprises the enhanced GFP (eGFP).

In some embodiments, the expression vector or plasmid further comprises at least one additional regulatory element. In some embodiments, the at least one regulatory element is selected from: SV40, puromycin resistance gene, weak positive element (WPE), a bacterial origin of replication (e.g., pUC ori), ampicillin resistance gene, 5' LTR (e.g., U5/RSV), reverse response element (RRE), central polypurine tract (cPPT), or any combination thereof.

In some embodiments, the expression vector or plasmid disclosed herein, is for use as an immunosensor. In some embodiments, the expression vector or plasmid disclosed herein, is for use in determining the expression levels of PD-L1.

In some embodiments, the expression vector or plasmid comprises the nucleic acid sequence:

```
                                          (SEQ ID NO: 1)
AGCCACCATGGTGAGCAAGGGCGAGGAGCTGTTCACCGGGG

TGGTGCCCATCCTGGTCGAGCTGGACGGCGACGTAAACGG

CCACAAGTTCAGCGTGTCCGGCGAGGGCGAGGGCGATGCC

ACCTACGGCAAGCTGACCCTGAAGTTCATCTGCACCACCG

GCAAGCTGCCCGTGCCCTGGCCCACCCTCGTGACCACCCT

GACCTACGGCGTGCAGTGCTTCAGCCGCTACCCCGACCAC

ATGAAGCAGCACGACTTCTTCAAGTCCGCCATGCCCGAAG

GCTACGTCCAGGAGCGCACCATCTTCTTCAAGGACGACGG

CAACTACAAGACCCGCGCCGAGGTGAAGTTCGAGGGCGAC

ACCCTGGTGAACCGCATCGAGCTGAAGGGCATCGACTTCA

AGGAGGACGGCAACATCCTGGGGCACAAGCTGGAGTACAA

CTACAACAGCCACAACGTCTATATCATGGCCGACAAGCAG

AAGAACGGCATCAAGGTGAACTTCAAGATCCGCCACAACA

TCGAGGACGGCAGCGTGCAGCTCGCCGACCACTACCAGCA

GAACACCCCCATCGGCGACGGCCCCGTGCTGCTGCCCGAC

AACCACTACCTGAGCACCCAGTCCGCCCTGAGCAAAGACC

CCAACGAGAAGCGCGATCACATGGTCCTGCTGGAGTTCGT

GACCGCCGCCGGGATCACTCTCGGCATGGACGAGCTGTAC

AAGTAGCTCGAGCTGTGGAATGTGTGTCAGTTAGGGTGTG

GAAAGTCCCCAGGCTCCCCAGCAGGCAGAAGTATGCAAAG

CATGCATCTCAATTAGTCAGCAACCAGGTGTGGAAAGTCC

CCAGGCTCCCCAGCAGGCAGAAGTATGCAAAGCATGCATC

TCAATTAGTCAGCAACCATAGTCCCGCCCCTAACTCCGCC

CATCCCGCCCCTAACTCCGCCCAGTTCCGCCCATTCTCCG

CCCCATGGCTGACTAATTTTTTTTATTTTATGCAGAGGCCG

AGGCCGCCTCTGCCTCTGAGCTATTCCAGAAGTAGTGAGG

AGGCTTTTTTGGAGGCCTAGGCTTTTGCAAAAAGCTCCCG

GGAGCTTGTATATCCATTTTCGGATCTGATCGGCGCGGGC

CGCGATCCCGCCCCTCTCCCTCCCCCCCCCCTAACGTTAC

TGGCCGAAGCCGCTTGGAATAAGGCCGGTGTGCGTTTGTC
```

-continued

```
TATATGTTATTTTCCACCATATTGCCGTCTTTTGGCAATG

TGAGGGCCCGGAAACCTGGCCCTGTCTTCTTGACGAGCAT

TCCTAGGGGTCTTTCCCCTCTCGCCAAAGGAATGCAAGGT

CTGTTGAATGTCGTGAAGGAAGCAGTTCCTCTGGAAGCTT

CTTGAAGACAAACAACGTCTGTAGCGACCCTTTGCAGGCA

GCGGAACCCCCCACCTGGCGACAGGTGCCTCTGCGGCCAA

AAGCCACGTGTATAAGATACACCTGCAAAGGCGGCACAAC

CCCAGTGCCACGTTGTGAGTTGGATAGTTGTGGAAAGAGT

CAAATGGCTCTCCTCAAGCGTATTCAACAAGGGGCTGAAG

GATGCCCAGAAGGTACCCCATTGTATGGGATCTGATCTGG

GGCCTCGGTGCACATGCTTTACATGTGTTTAGTCGAGGTT

AAAAAAACGTCTAGGCCCCCCGAACCACGGGGACGTGGTT

TTCCTTTGAAAAACACGATGATAAGCTTGCCACAACCCAC

AAGGAGACGACCTTCCATGACCGAGTACAAGCCCACGGTG

CGCCTCGCCACCCGCGACGACGTCCCCCGGGCCGTACGCA

CCCTCGCCGCCGCGTTCGCCGACTACCCCGCCACGCGCCA

CACCGTCGACCCGGACCGCCACATCGAGCGGGTCACCGAG

CTGCAAGAACTCTTCCTCACGCGCGTCGGGCTCGACATCG

GCAAGGTGTGGGTCGCGGACGACGGCGCCGCGGTGGCGGT

CTGGACCACGCCGGAGAGCGTCGAAGCGGGGGCGGTGTTC

GCCGAGATCGGCCCGCGCATGGCCGAGTTGAGCGGTTCCC

GGCTGGCCGCGCAGCAACAGATGGAAGGCCTCCTGGCGCC

GCACCGGCCCAAGGAGCCCGCGTGGTTCCTGGCCACCGTC

GGCGTCTCGCCCGACCACCAGGGCAAGGGTCTGGGCAGCG

CCGTCGTGCTCCCCGGAGTGGAGGCGGCCGAGCGCGCCGG

GGTGCCCGCCTTCCTGGAGACCTCCGCGCCCCGCAACCTC

CCCTTCTACGAGCGGCTCGGCTTCACCGTCACCGCCGACG

TCGAGGTGCCCGAAGGACCGCGCACCTGGTGCATGACCCG

CAAGCCCGGTGCCTAGACGCGTCTGGAACAATCAACCTCT

GGATTACAAAATTTGTGAAAGATTGACTGGTATTCTTAAC

TATGTTGCTCCTTTTACGCTATGTGGATACGCTGCTTTAA

TGCCTTTGTATCATGCTATTGCTTCCCGTATGGCTTTCAT

TTTCTCCTCCTTGTATAAATCCTGGTTGCTGTCTCTTTAT

GAGGAGTTGTGGCCCGTTGTCAGGCAACGTGGCGTGGTGT

GCACTGTGTTTGCTGACGCAACCCCCACTGGTTGGGGCAT

TGCCACCACCTGTCAGCTCCTTTCCGGGACTTTCGCTTTC

CCCCTCCCTATTGCCACGCGGCGGAACTCATCGCCGCCTGCC

TTGCCCGCTGCTGGACAGGGGCTCGGCTGTTGGGCACTGA

CAATTCCGTGGTGTTGTCGGGGAAGCTGACGTCCTTTCCA

TGGCTGCTCGCCTGTGTTGCCACCTGGATTCTGCGCGGGA

CGTCCTTCTGCTACGTCCCTTCGGCCCTCAATCCAGCGGA
```

-continued

```
CCTTCCTTCCCGCGGCCTGCTGCCGGCTCTGCGGCCTCTT

CCGCGTCTTCGCCTTCGCCCTCAGACGAGTCGGATCTCCC

TTTGGGCCGCCTCCCCGCCTGGAATTAATTCTGCAGTCGA

GACCTAGAAAAACATGGAGCAATCACAAGTAGCAATACAG

CAGCTACCAATGCTGATTGTGCCTGGCTAGAAGCACAAGA

GGAGGAGGAGGTGGGTTTTTCCAGTCACACCTCAGGACCT

TTAAGACCAATGACTTACAAGGCAGCTGTAGATCTTAGCC

ACTTTTTAAAAGAAAAGAGGGGACTGGAAGGGCTAATTCA

CTCCCAACGAAGACAAGATCTGCTTTTTGCCTGTACTGGG

TCTCTCTGGTTAGACCAGATCTGAGCCTGGGAGCTCTCTG

GCTAACTAGGGAACCCACTGCTTAAGCCTCAATAAAGCTT

GCCTTGAGTGCTTCAAGTAGTGTGTGCCCGTCTGTTGTGT

GACTCTGGTAACTAGAGATCCCTCAGACCCTTTTAGTCAG

TGTGGAAAATCTCTAGCAGTAGTAGTTCATGTCATCTTAT

TATTCAGTATTTATAACTTGCAAAGAAATGAATATCAGAG

AGTGAGAGGCTAGCGTTTTACCGTCGACCTCTAGCTAGAG

CTTGGCGTAATCATGGTCATAGCTGTTTCCTGTGTGAAAT

TGTTATCCGCTCACAATTCCACACAACATACGAGCCGGAA

GCATAAAGTGTAAAGCCTGGGGTGCCTAATGAGTGAGCTA

ACTCACATTAATTGCGTTGCGCTCACTGCCCGCTTTCCAG

TCGGGAAACCTGTCGTGCCAGCTGCATTAATGAATCGGCC

AACGCGCGGGGAGAGGCGGTTTGCGTATTGGGCGCTCTTC

CGCTTCCTCGCTCACTGACTCGCTGCGCTCGGTCGTTCGG

CTGCGGCGAGCGGTATCAGCTCACTCAAAGGCGGTAATAC

GGTTATCCACAGAATCAGGGGATAACGCAGGAAAGAACAT

GTGAGCAAAAGGCCAGCAAAAGGCCAGGAACCGTAAAAAG

GCCGCGTTGCTGGCGTTTTTCCATAGGCTCCGCCCCCCTG

ACGAGCATCACAAAAATCGACGCTCAAGTCAGAGGTGGCG

AAACCCGACAGGACTATAAAGATACCAGGCGTTTCCCCCT

GGAAGCTCCCTCGTGCGCTCTCCTGTTCCGACCCTGCCGC

TTACCGGATACCTGTCCGCCTTTCTCCCTTCGGGAAGCGT

GGCGCTTTCTCATAGCTCACGCTGTAGGTATCTCAGTTCG

GTGTAGGTCGTTCGCTCCAAGCTGGGCTGTGTGCACGAAC

CCCCCGTTCAGCCCGACCGCTGCGCCTTATCCGGTAACTA

TCGTCTTGAGTCCAACCCGGTAAGACACGACTTATCGCCA

CTGGCAGCAGCCACTGGTAACAGGATTAGCAGAGCGAGGT

ATGTAGGCGGTGCTACAGAGTTCTTGAAGTGGTGGCCTAA

CTACGGCTACACTAGAAGAACAGTATTTGGTATCTGCGCT

CTGCTGAAGCCAGTTACCTTCGGAAAAAGAGTTGGTAGCT

CTTGATCCGGCAAACAAACCACCGCTGGTAGCGGTTTTTT
```

-continued

```
TGTTTGCAAGCAGCAGATTACGCGCAGAAAAAAAGGATCT

CAAGAAGATCCTTTGATCTTTTCTACGGGGTCTGACGCTC

AGTGGAACGAAAACTCACGTTAAGGGATTTTGGTCATGAG

ATTATCAAAAAGGATCTTCACCTAGATCCTTTTAAATTAA

AAATGAAGTTTTAAATCAATCTAAAGTATATATGAGTAAA

CTTGGTCTGACAGTTACCAATGCTTAATCAGTGAGGCACC

TATCTCAGCGATCTGTCTATTTCGTTCATCCATAGTTGCC

TGACTCCCCGTCGTGTAGATAACTACGATACGGGAGGGCT

TACCATCTGGCCCCAGTGCTGCAATGATACCGCGAGACCC

ACGCTCACCGGCTCCAGATTTATCAGCAATAAACCAGCCA

GCCGGAAGGGCCGAGCGCAGAAGTGGTCCTGCAACTTTAT

CCGCCTCCATCCAGTCTATTAATTGTTGCCGGGAAGCTAG

AGTAAGTAGTTCGCCAGTTAATAGTTTGCGCAACGTTGTT

GCCATTGCTACAGGCATCGTGGTGTCACGCTCGTCGTTTG

GTATGGCTTCATTCAGCTCCGGTTCCCAACGATCAAGGCG

AGTTACATGATCCCCCATGTTGTGCAAAAAAGCGGTTAGC

TCCTTCGGTCCTCCGATCGTTGTCAGAAGTAAGTTGGCCG

CAGTGTTATCACTCATGGTTATGGCAGCACTGCATAATTC

TCTTACTGTCATGCCATCCGTAAGATGCTTTTCTGTGACT

GGTGAGTACTCAACCAAGTCATTCTGAGAATAGTGTATGC

GGCGACCGAGTTGCTCTTGCCCGGCGTCAATACGGGATAA

TACCGCGCCACATAGCAGAACTTTAAAAGTGCTCATCATT

GGAAAACGTTCTTCGGGGCGAAAACTCTCAAGGATCTTAC

CGCTGTTGAGATCCAGTTCGATGTAACCCACTCGTGCACC

CAACTGATCTTCAGCATCTTTTACTTTCACCAGCGTTTCT

GGGTGAGCAAAAACAGGAAGGCAAAATGCCGCAAAAAAGG

GAATAAGGGCGACACGGAAATGTTGAATACTCATACTCTT

CCTTTTTCAATATTATTGAAGCATTTATCAGGGTTATTGT

CTCATGAGCGGATACATATTTGAATGTATTTAGAAAAATA

AACAAATAGGGGTTCCGCGCACATTTCCCCGAAAAGTGCC

ACCTGACGTCGACGGATCGGGAGATCAACTTGTTTATTGC

AGCTTATAATGGTTACAAATAAAGCAATAGCATCACAAAT

TTCACAAATAAAGCATTTTTTTCACTGCATTCTAGTTGTG

GTTTGTCCAAACTCATCAATGTATCTTATCATGTCTGGAT

CAACTGGATAACTCAAGCTAACCAAAATCATCCCAAACTT

CCCACCCCATACCCTATTACCACTGCCAATTACCCTGTGG

GCGCAATTAACCCTCACTAAAGGGAACAAAAGCTGGAGCT

GCAAGCTTAATGTAGTCTTATGCAATACTCTTGTAGTCTT

GCAACATGGTAACGATGAGTTAGCAACATGCCTTACAAGG

AGAGAAAAAGCACCGTGCATGCCGATTGGTGGAAGTAAGG

TGGTACGATCGTGCCTTATTAGGAAGGCAACAGACGGGTC
```

-continued

```
TGACATGGATTGGACGAACCACTGAATTGCCGCATTGCAG

AGATATTGTATTTAAGTGCCTAGCTCGATACATAAACGGG

TCTCTCTGGTTAGACCAGATCTGAGCCTGGGAGCTCTCTG

GCTAACTAGGGAACCCACTGCTTAAGCCTCAATAAAGCTT

GCCTTGAGTGCTTCAAGTAGTGTGTGCCCGTCTGTTGTGT

GACTCTGGTAACTAGAGATCCCTCAGACCCTTTTAGTCAG

TGTGGAAAATCTCTAGCAGTGGCGCCCGAACAGGGACTTG

AAAGCGAAAGGGAAACCAGAGGAGCTCTCTCGACGCAGGA

CTCGGCTTGCTGAAGCGCGCACGGCAAGAGGCGAGGGGCG

GCGACTGGTGAGTACGCCAAAAATTTTGACTAGCGGAGGC

TAGAAGGAGAGAGATGGGTGCGAGAGCGTCAGTATTAAGC

GGGGGAGAATTAGATCGCGATGGGAAAAAATTCGGTTAAG

GCCAGGGGGAAAGAAAAAATATAAATTAAAACATATAGTA

TGGGCAAGCAGGGAGCTAGAACGATTCGCAGTTAATCCTG

GCCTGTTAGAAACATCAGAAGGCTGTAGACAAATACTGGG

ACAGCTACAACCATCCCTTCAGACAGGATCAGAAGAACTT

AGATCATTATATAATACAGTAGCAACCCTCTATTGTGTGC

ATCAAAGGATAGAGATAAAAGACACCAAGGAAGCTTTAGA

CAAGATAGAGGAAGAGCAAAACAAAAGTAAGACCACCGCA

CAGCAAGCGGCCGGCCGCTGATCTTCAGACCTGGAGGAGG

AGATATGAGGGACAATTAATTGGAGAAGTGAATTATATAA

ATATAAAGTAGTAAAAATTGAACCATTAGGAGTAGCACCC

ACCAAGGCAAAGAGAAGAGTGGTGCAGAGAGAAAAAAGAG

CAGTGGGAATAGGAGCTTTGTTCCTTGGGTTCTTGGGAGC

AGCAGGAAGCACTATGGGCGCAGCGTCAATGACGCTGACG

GTACAGGCCAGACAATTATTGTCTGGTATAGTGCAGCAGC

AGAACAATTTGCTGAGGGCTATTGAGGCGCAACAGCATCT

GTTGCAACTCACAGTCTGGGGCATCAAGCAGCTCCAGGCA

AGAATCCTGGCTGTGGAAAGATACCTAAAGGATCAACAGC

TCCTGGGGATTTGGGGTTGCTCTGGAAAACTCATTTGCAC

CACTGCTGTGCCTTGGAATGCTAGTTGGAGTAATAAATCT

CTGGAACAGATTTGGAATCACACGACCTGGATGGAGTGGG

ACAGAGAAATTAACAATTACACAAGCTTAATACACTCCTT

AATTGAAGAATCGCAAAACCAGCAAGAAAGAATGAACAA

GAATTATTGGAATTAGATAAATGGGCAAGTTTGTGGAATT

GGTTTAACATAACAAATTGGCTGTGGTATATAAAATTATT

CATAATGATAGTAGGAGGCTTGGTAGGTTTAAGAATAGTT

TTTGCTGTACTTTCTATAGTGAATAGAGTTAGGCAGGGAT

ATTCACCATTATCGTTTCAGACCCACCTCCCAACCCCGAG

GGGACCCGACAGGCCCGAAGGAATAGAAGAAGAAGGTGGA
```

-continued

```
GAGAGAGACAGAGACAGATCCATTCGATTAGTGAACGGAT

CTCGACGGTATCGCCTTTAAAAGAAAAGGGGGGATTGGGG

GGTACAGTGCAGGGGAAAGAATAGTAGACATAATAGCAAC

AGACATACAAACTAAAGAACTACAAAAACAAATTACAAAA

ATTCAAAATTTTCGGGTTTATTACAGGGACAGCAGAGATC

CAGTTTATCTAATACGACTCACTATAGGGAGAGAGAGAGA

ATTACCCTCACTAAAGGGAGGAGAAGCATGAATTGAAGGA

GATAGAACCAGATCTTGGAATTCACTAAGCCAGCGGACAC

CCCAGTATTCACCCAGTGCACTACTTTGGAATAGTAGTTT

TGTAAGTAAGTGGGGGAAAGCAGAGAATGAAGAAGGCCCT

TGAAGTCCAACAGTGAAATGTTTAAAGATGACAGTGCTCT

GTGGAGTTCCCAAGGTTTTGTCTTGGAAAAAGTCCACACT

TCCAGTTCGCAGAAAGTCTTTCTCAACATCATTTAGAATA

GACTTCCCCCACCTGGATCCCGAGACTGGCCGTGATCCAC

AGCGTTCACAAAGGGCACGGTTCGAGATGGGAAGTTCTTG

AACGGCAAGACAACTGGTTTCATTATGTCGAGGAACTTTG

AGGAAGTCACCAAATCCACGATTTAAAAATATATTTCCTA

TTATACAGACACACCTACTTTCTAGAATTAAAACTGAGTC

ATTTGCTTGATATTAACTCTATAGGTTGTATAACTCTATA

TGTAAAGTCATGTCAAGACTGTCACGTATCCACGTATCCA

GAAAGGGCTTGAAAGAGATGGGGAATCGGATGGTAATTTG

AAGTGTCTGGATTCTGAAGATAAAATTTAAGTCAGAGATC

TTATGACTTCAGATATTTTGCTTCTAAAGCGCTCACTGCT

CAAGCCTGAAGATTTGAAATTCGGGTCCTCATTACCCATA

ATAAATGCAGTGATGGCCCATTTCTGAGACCCTAGCCCTG

GCAGCAGGGGCGCGGATGGGGATCCCTGGACCACGCTGGC

CGGCTAGTTTGGCCAGCTGCGAGCCCGAGGTTAGGTAAGA

GAGACCCTCTTTCAAAAATCAAGGTGGGAGCTGTAGAGGA

AGGCAACCTATGTGGATCTCCAAGCACACGCTCCCCCCCA

CCCCCACCCCCGACCTCAGGTTCCACTCCCACCCAAAATA

GAGCTGAGTTGTTTACTCTGGACTGTTTCTTTGAGGGAAC

CTGATTTACAAGAAAGCTAATGCAGGTTTCACTTTCACTT

TTAGTTTCGTTTTTAAATAGTGTTTGTTTGTTTTTGTTTT

TATCGACAGCCTCTCAGTAGCAGCCCGGTTGTCTTGGAGC

TCTCTCTATAGACCAGAGACTCACCTGCCACTGGCTCCTG

AGTACTGGAATTAAGGCGTGTGTCACCGCACCGAAGCCTA

GTTTCGTTTTTTCTTAAACTGTGAATATCCCAAAGCTGAC

TCTAAAGTCATCCGCAGGAAATACTATGAGATAAACTCAT

GCTCAAAGGGACTGGGTGGCTTCGGTTTCACAGACAGCGG

AGGTTGGACAAGGCTTCCGCGGAGTGGGCGGGGCTCTGAA

CTCGAGATAAGACCAGGAAATCGTGGTCCCCAAGCCTCAT
```

-continued

```
GCCAGGCTGCACTTGCACGTCGCGGGCCAGTCTCCTCGCC

TGCAGGTAAGGGAGCATCTTCTCGCGGAATCCGCTTGCAG

GGCACTTTAAAGAGCCAGAATCCCTAGACCTTTTTAGGAC

GGAGAAGGGAACCGGTTTCCTGGGAAAGTTAAGAACTCAG

AATCCGCAGTTTTGTGTGTTTATGGATCTTGTGGGTAGGT

AGCTGGGTCAGAAGAGATGAATTAATTGGTCCTAGCGCGA

CTTGACTGTTTGCTAAGCTTGGTACCGAGCTCGGATCC.
```

As used herein, the term "about" when combined with a value refers to plus and minus 10% of the reference value. For example, a length of about 1,000 nanometers (nm) refers to a length of 1,000 nm±100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Various embodiments and aspects of the present invention as delineated hereinabove and as claimed in the claims section below find experimental support in the following examples.

EXAMPLES

Generally, the nomenclature used herein, and the laboratory procedures utilized in the present invention include chemical, molecular, biochemical, and cell biology tech-
niques. Such techniques are thoroughly explained in the
literature. See, for example, "Molecular Cloning: A labora-
tory Manual" Sambrook et al., (1989); "Current Protocols in
Molecular Biology" Volumes I-III Ausubel, R. M., ed.
(1994); "Cell Biology: A Laboratory Handbook", Volumes
I-III Cellis, J. E., ed. (1994); The Organic Chemistry of
Biological Pathways by John McMurry and Tadhg Begley
(Roberts and Company, 2005); Organic Chemistry of
Enzyme-Catalyzed Reactions by Richard Silverman (Aca-
demic Press, 2002); Organic Chemistry (6$^{th}$ Edition) by
Leroy "Skip" G Wade; Organic Chemistry by T. W. Graham
Solomons and, Craig Fryhle.

Materials and Methods

Cloning Procedure

Recombinant lentiviral particles were generated by trans-
fecting a lentiviral expression plasmid into lentiviral pack-
aging cells. The lentiviral expression plasmid contained a
PD-L1 signaling or pathway responsive element, including
all other elements required for packaging, transduction and
stable integration of the viral expression construct into
genomic DNA, which further enable expression of elements
carried by the vector. Further, the expression plasmid con-
tained a reporter gene, e.g., eGFP, the expression of which
is indicative of activation of the above-mentioned PD-L1
signaling responsive element.

Generation of Expressing Cells

Transfection

The chosen tumor cells for the viral infection were
LivMet cells. LivMet cells are a pancreatic tumor cell line
derived from KrasG12D/+ transgenic mice which developed
tumor of pancreatic ductal adenocarcinoma (PDA). The
LivMet cell line was derived from a liver metastasis that
occurred in these transgenic mice.

Two days before infection, $1×10^5$ LivMet cells were
seeded in a 48 well plate in 600 μl DMEM supplemented
with 10% heat-inactivated fetal bovine serum so that the
cells were 70-80% confluent in the moment of infection. The
cells were incubated at 37° C. with 5% $CO_2$. 1.5 μl of 2.82
μl $10^8$ TU/ml titer lentivirus particles were added into the
culture following changing the medium to 200 μl DMEM
containing 1% heat-inactivated fetal bovine serum. Culture
was incubated in 37° C. with 5% $CO_2$ for 4 hours and 400
μl of 10% heat-inactivated fetal bovine serum DMEM was
added.

Figure 12:
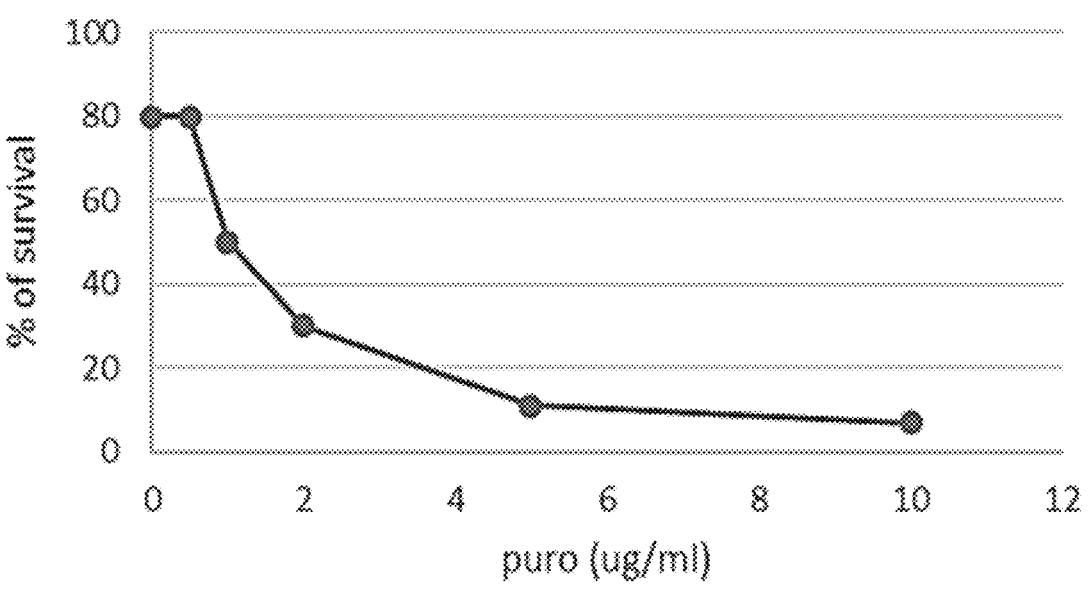
FIG. 12 includes a plot showing the survival % of LivMet cells according to their reaction to different concentrations of puromycin.

Two (2) days after infection, 3 μg/ml of puromycin was
used to select the infected cells according to the puromycin
survival tests on LivMet cells (FIG. 12).

Figure 13:
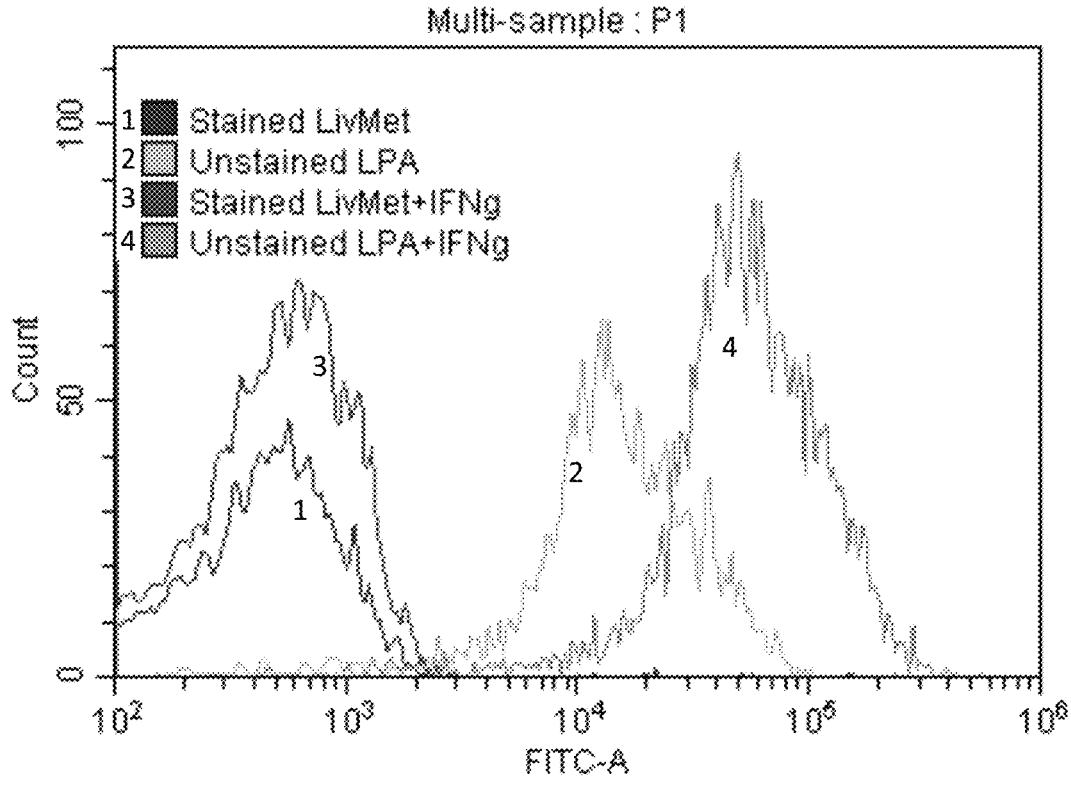
FIG. 13 includes a graph showing the fluorescent intensity of eGFP in LivMet and LPA cells, untreated and treated with IFNγ.
Figure 14:
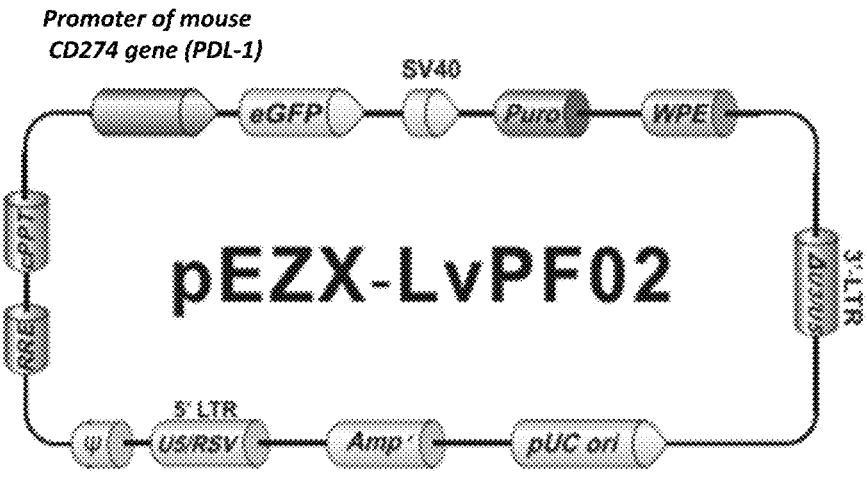
FIG. 14 includes scheme of a non-limiting representation of an immunosensor comprising a promoter of mouse CD274 gene (PDL-1) cloned into lentiviral vector pEZX-LvPF02 vector.

In order to obtain 1 clone, the inventors performed a
single cell cloning by seeding 0.5 cell per well in ten 96-well
plates. Then, using a light microscope, the inventors chose
the clones that expressed the least eGFP and checked these
clones for PD-L1 protein expression after IFN-γ stimulation
via fluorescence activated cell sorting (FACS). The clone
that had the highest eGFP MFI only after IFN-γ stimulation
(LPA) was chosen (FIG. 13).

Expression Analysis $1×10^5$ LPA cells were seeded in 4×96 well plates one day
before treatment. Each well was treated with 10 mM of a
different FDA approved drug. DiscoveryProbe™ FDA-ap-
proved Drug Library was purchased from ApexBio com-
pany. Two (2) plates were treated with IFN-γ, and 2 were
not. One plate of each was measured for eGFP MFI in FACS
24 hours after treatment and the other was tested 48 hours
after treatment. Each plate had 8 wells of CTRL: 2×LivMet,
2×LivMet+IFN-γ, 2×LPA, and 2×LPA-γ.

Validation of drugs that upregulated or downregulated
eGFP expression in this screening was performed on LivMet
cells. $1×10^5$ LivMet cells were seeded in two 96 well plates
one day before treatment. Each well was treated with a
chosen drug and cells were stained with anti PD-L1 anti-
body, 24 hr and 48 hr after treatment with or without IFN-γ.
Supernatant of each well was further tested via ELISA for
CXCL10 expression.

Figure 1B:
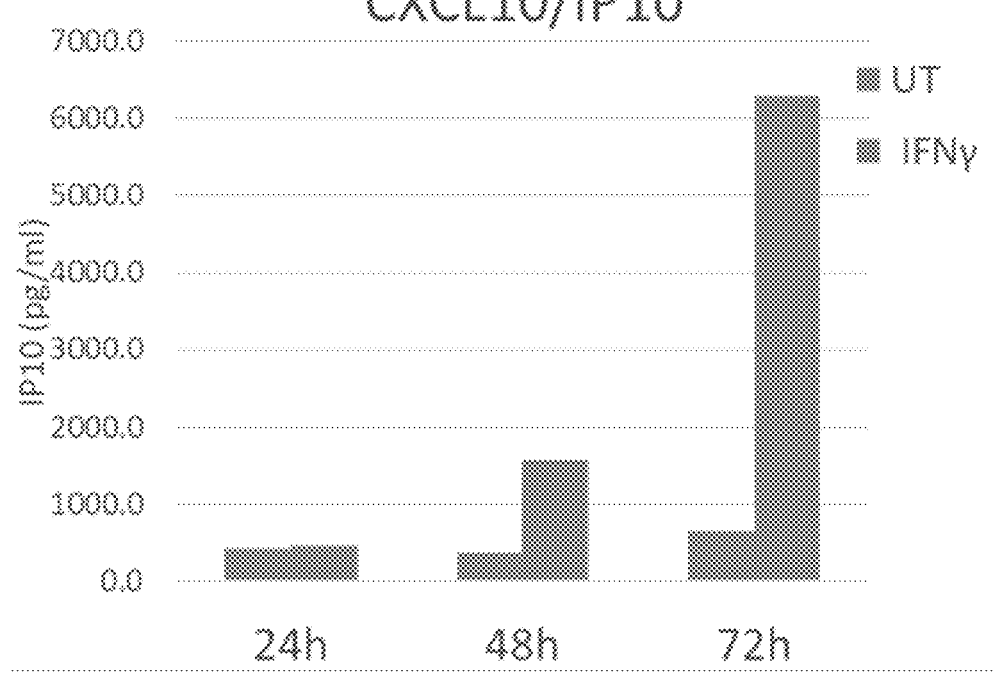

FIGS. 1A-1B include vertical bar graphs showing the
expression levels of PD-L1 (1A) and CXCL10 (1B) in
LivMet cells in the absence (UT) or presence of interferon
γ (IFN-γ).

Figure 2:
FIG. 2 includes a graph showing the upregulating effect of IFN-γ and compound 18 on the expression of GFP in LPA cells.
Figure 2:
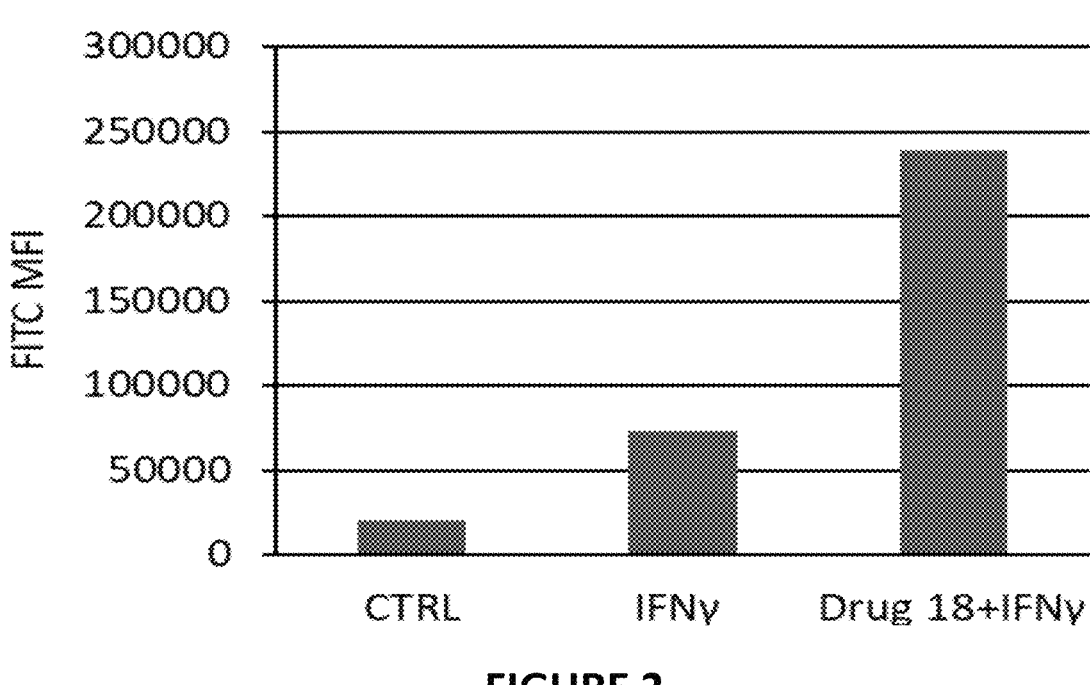

FIG. 2 includes a graph showing the upregulating effect of
IFN-γ and compound 18 on the expression of GFP in LPA
cells.

Figure 3A:
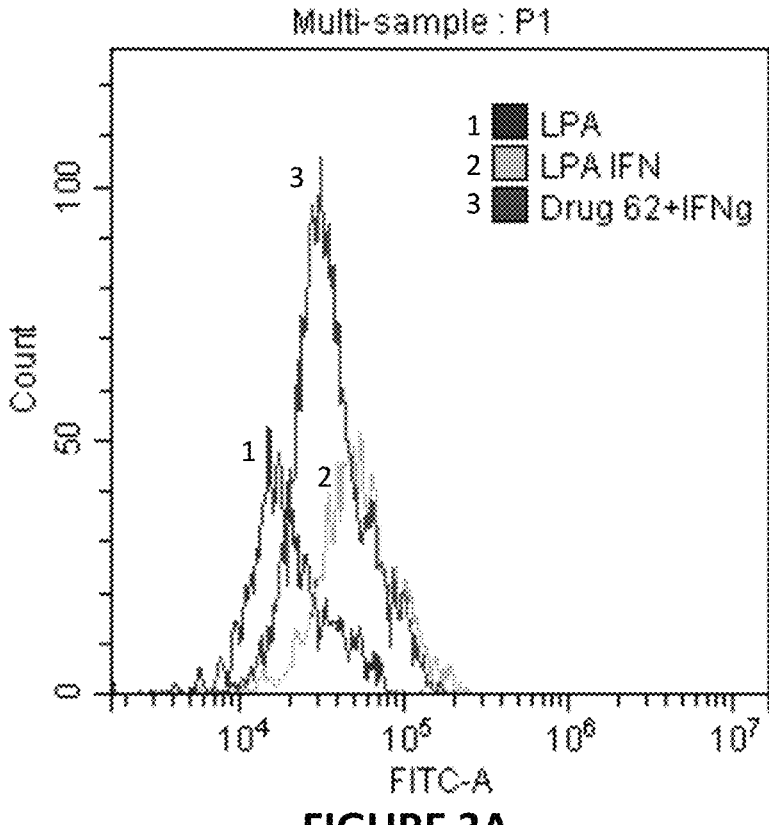
FIGS. 3A-3B include graphs showing the down-regulating effect of IFN-γ and compound 62 on the expression of GFP in LPA cells. (3A) a graph of a FACS analysis. (3B) a vertical bar graph showing the FITC MFI of the different experimental groups.
Figure 3B:
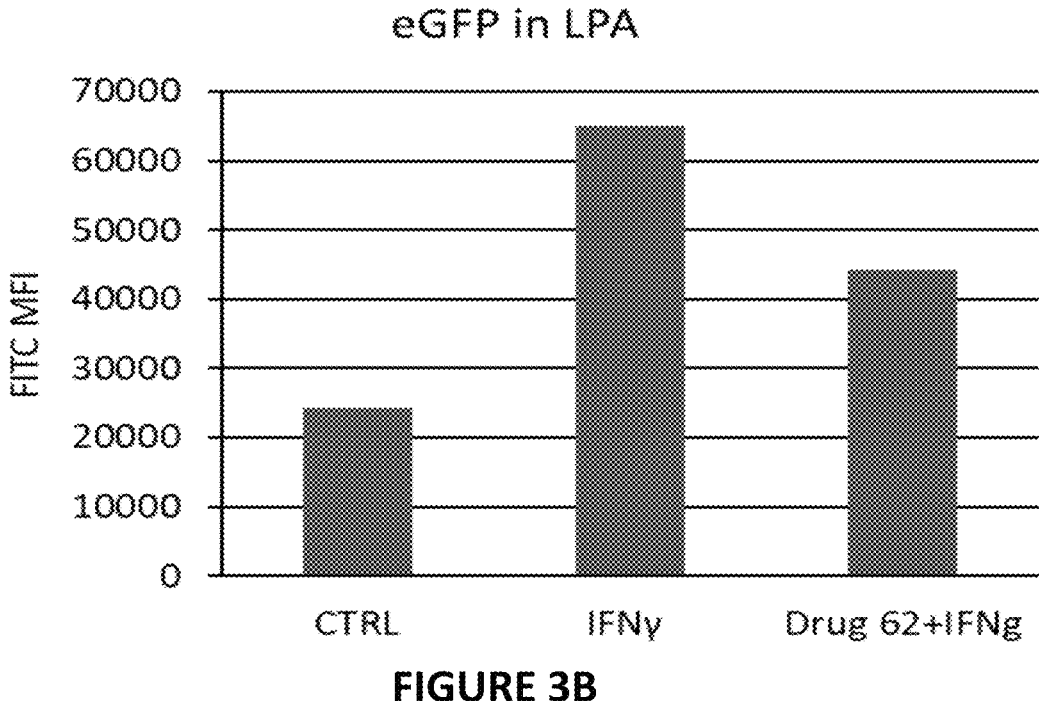

FIGS. 3A-3B include graphs showing the down-regulat-
ing effect of IFN-γ and compound 62 on the expression of
GFP in LPA cells. (3A) a graph of a FACS analysis. (3B) a
vertical bar graph showing the FITC MFI of the different
experimental groups.

Figure 4A:
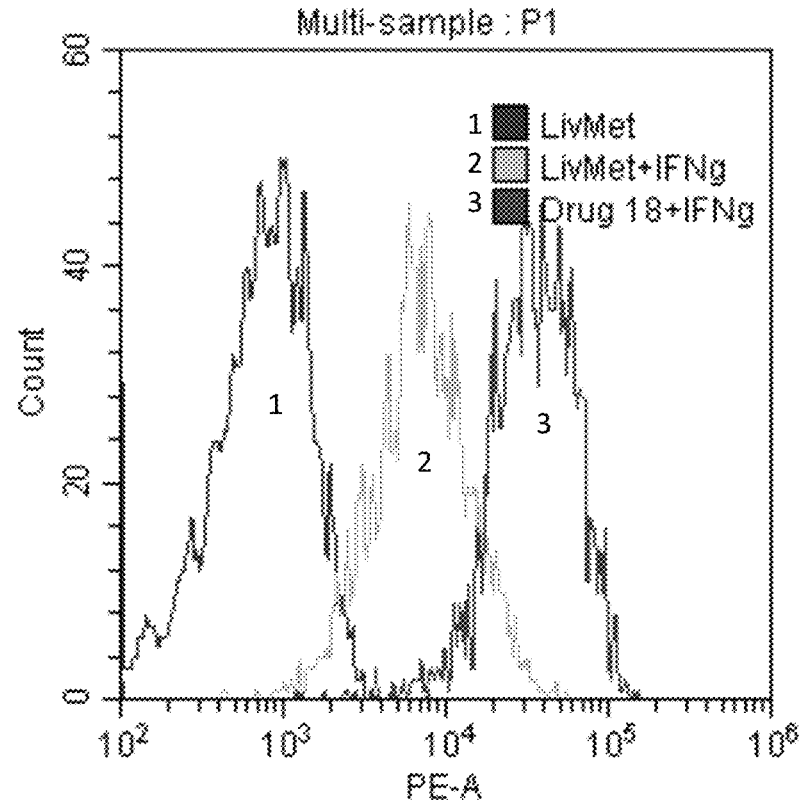
FIGS. 4A-4B include graphs showing a validation of the upregulating effect of IFN-γ and compound 18 on the expression of PD-L1 in LivMet cells. (4A) a graph of a FACS analysis. (4B) a vertical bar graph showing the PE MFI of the different experimental groups.
Figure 4B:
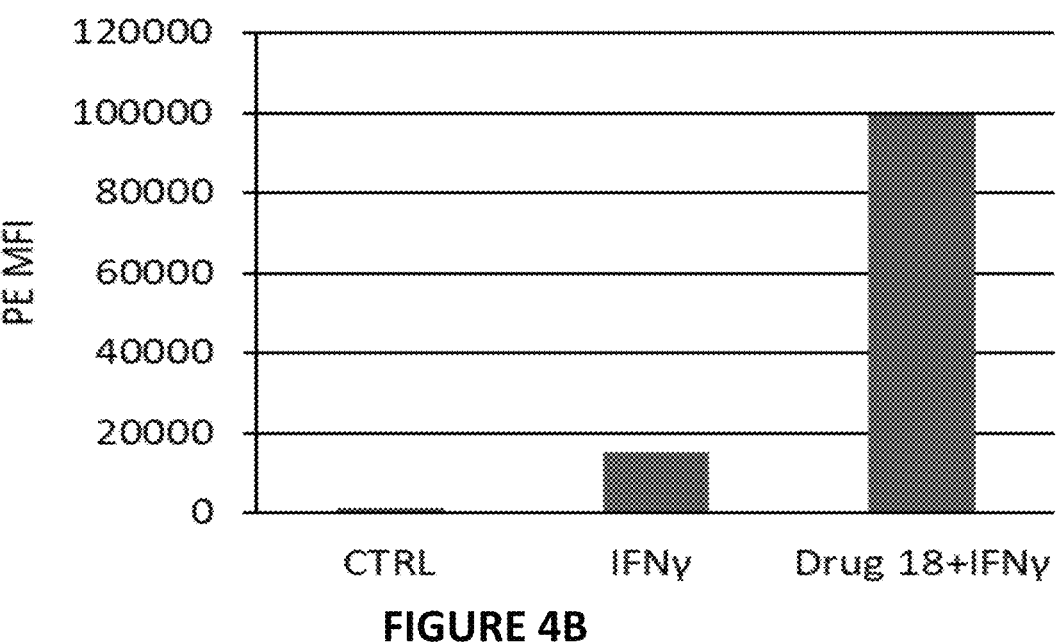

FIGS. 4A-4B include graphs showing a validation of the
upregulating effect of IFN-γ and compound 18 on the
expression of PD-L1 in LivMet cells. (4A) a graph of a
FACS analysis. (3B) a vertical bar graph showing the PE
MFI of the different experimental groups.

Figure 5:
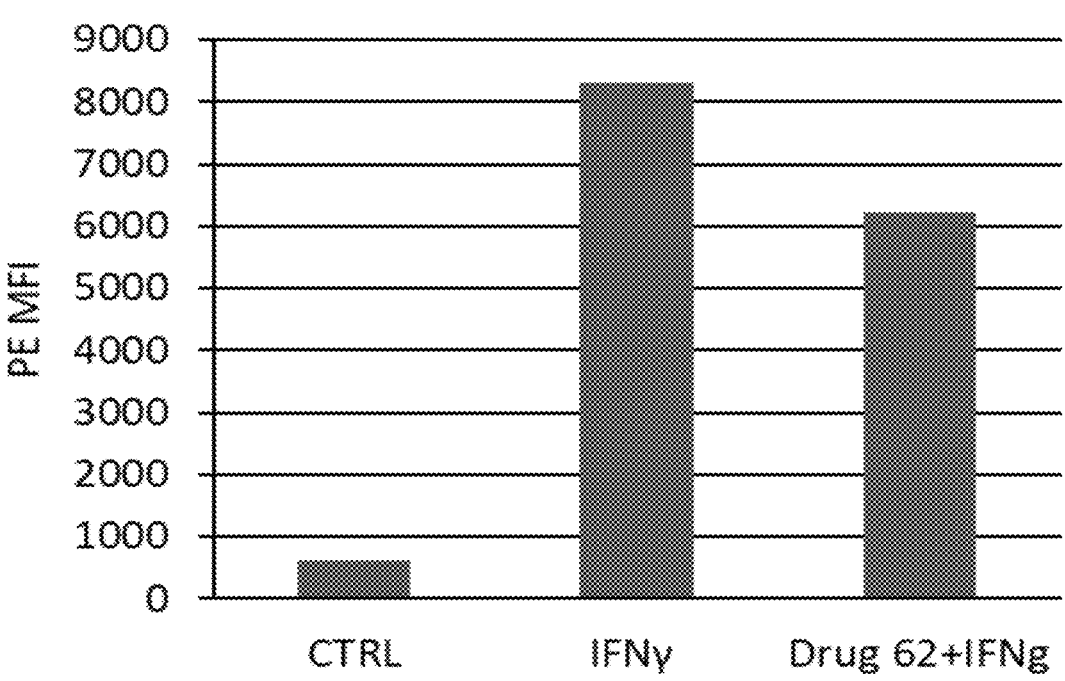
FIG. 5 includes a graph showing a validation of the down-regulating effect of IFN-γ and compound 62 on the expression of PD-L1 in LivMet cells.

FIG. 5 includes a graph showing a validation of the
down-regulating effect of IFN-γ and compound 62 on the
expression of PD-L1 in LivMet cells.

Figure 6:
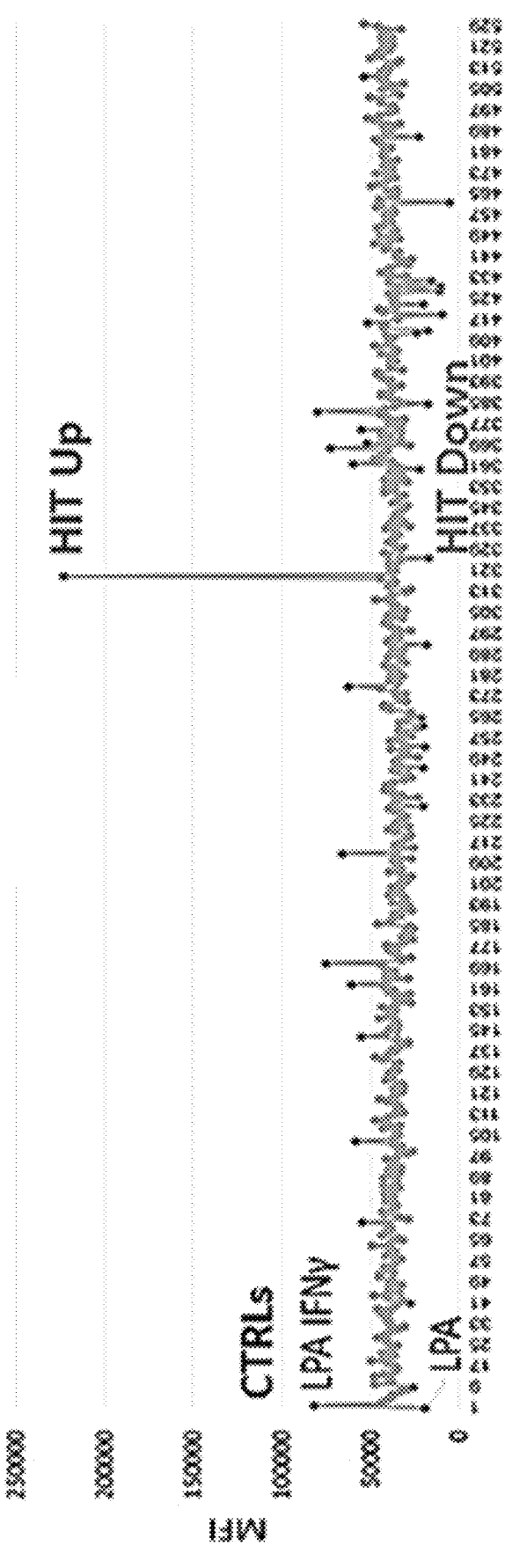
FIG. 6 includes a graph showing the effect of IFN-γ and a series of compounds (1-529) on the expression of GFP in LPA cells.

FIG. 6 includes a graph showing the effect of IFN-γ and
a series of compounds (1-529) on the expression of GFP in
LPA cells.

Figure 7:
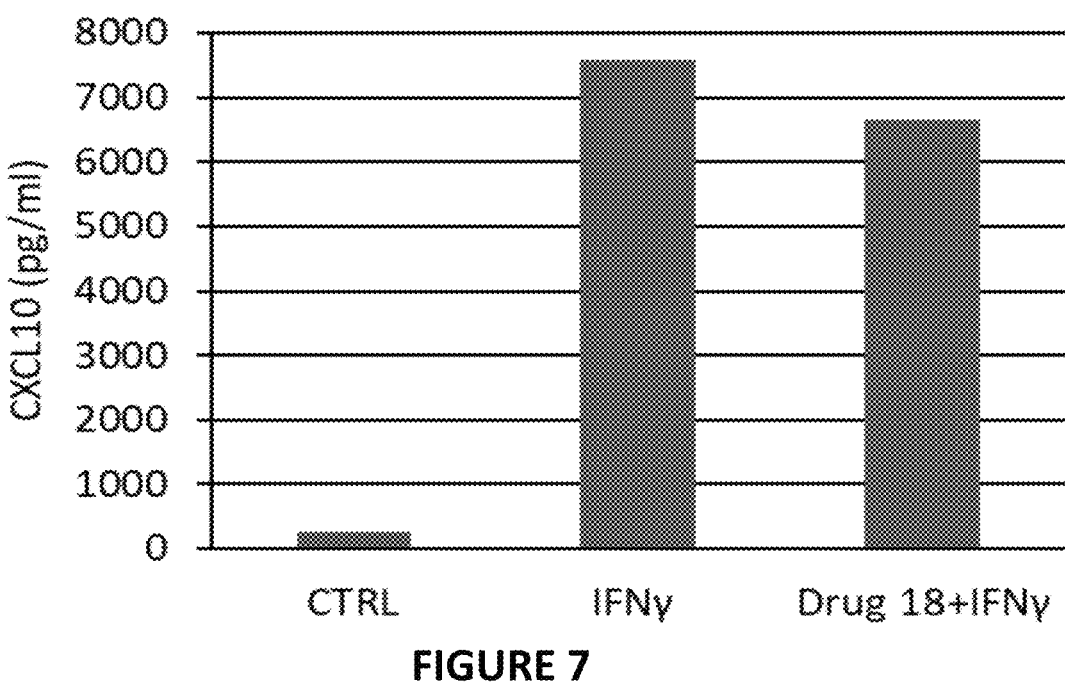
FIG. 7 includes a graph showing the effect of IFN-γ and compound 18 (which stimulates overexpression of PD-L1) on CXCL10 expression in LPA cells (Upregulation, minor down regulation).

FIG. 7 includes a graph showing the effect of IFN-γ and
compound 18 (which stimulates overexpression of PD-L1)
on CXCL10 expression in LPA cells (Upregulation, minor
down regulation).

Figure 8:
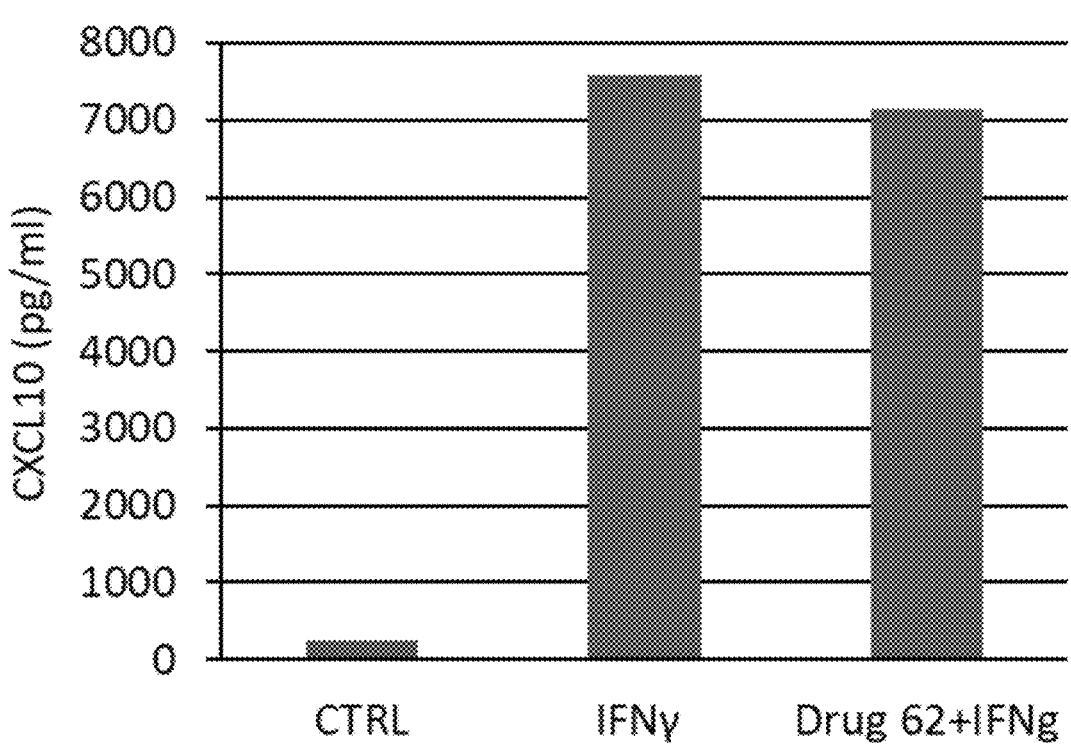
FIG. 8 includes a graph showing the effect of IFN-γ and compound 62 (which inhibits expression of PD-L1) on CXCL10 expression in LPA cells (Upregulation, minor downregulation).

FIG. 8 includes a graph showing the effect of IFN-γ and
compound 62 (which inhibits expression of PD-L1) on
CXCL10 expression in LPA cells (Upregulation, minor
downregulation).

Figure 9:
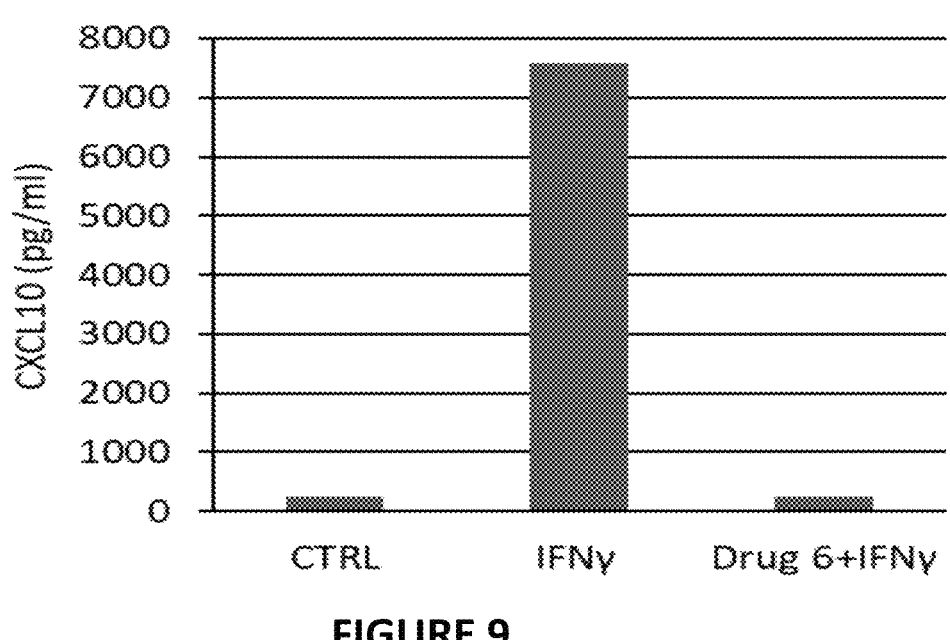
FIG. 9 includes a graph showing the effect of IFN-γ and compound 6 (which stimulates overexpression of PD-L1) on CXCL10 expression in LPA cells (Upregulation, Downregulation).

FIG. 9 includes a graph showing the effect of IFN-γ and
compound 6 (which stimulates overexpression of PD-L1) on
CXCL10 expression in LPA cells (Upregulation, Downregu-
lation).

Figure 10:
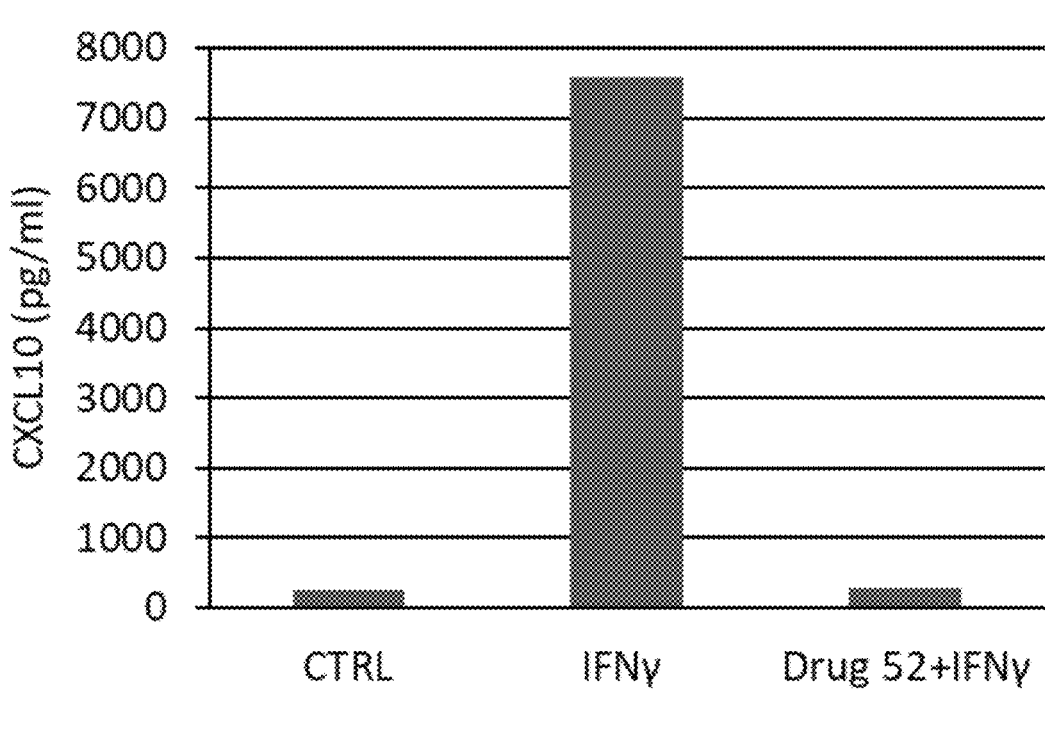
FIG. 10 includes a graph showing the effect of IFN-γ and compound 52 (which inhibits expression of PD-L1) on CXCL10 expression in LPA cells (Downregulation, Downregulation).

FIG. 10 includes a graph showing the effect of IFN-γ and
compound 52 (which inhibits expression of PD-L1) on
CXCL10 expression in LPA cells (Downregulation, Down-
regulation).

Figure 11:
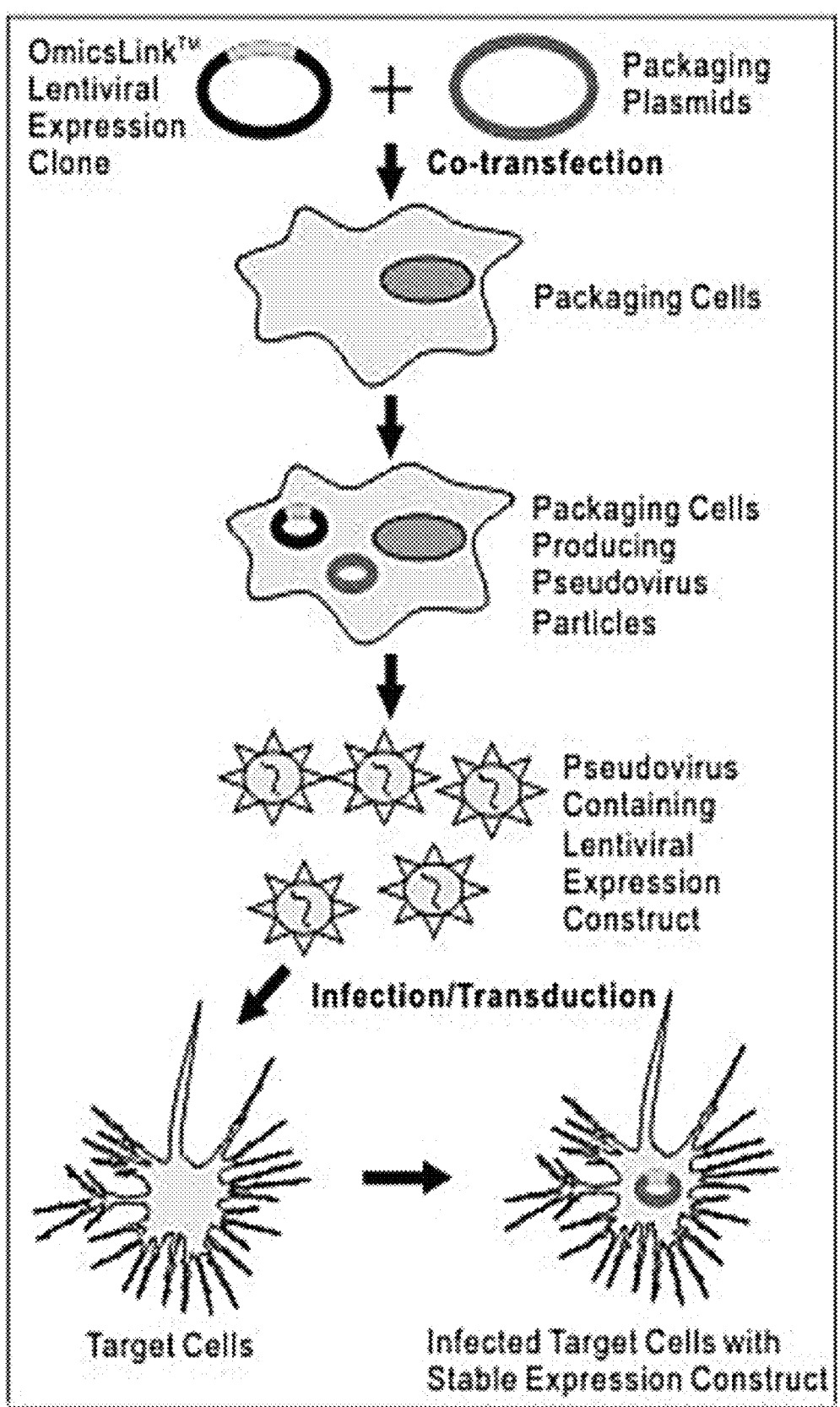
FIG. 11 includes a schematic non-limiting set up of lentivirus production and infection of target cells.

FIG. 11 includes a schematic non-limiting set up of
lentivirus production and infection of target cells.

FIG. 12 includes a plot showing the survival % of LivMet
cells according to their reaction to different concentrations
of puromycin.

FIG. 13 includes a graph showing the fluorescent intensity
of eGFP in LivMet and LPA cells, untreated and treated with
IFNγ.

Drugs that either reduced or enhanced GFP expression
were then validated for their effect on the expression of
IFN-g inducible genes in-vitro in mouse LivMet cells,
thereafter in human primary lung cells and in-vivo in a
mouse Delayed-type hypersensitivity (DTH) model.

Human Primary lung cells were isolated from normal lung
biopsies and culture for five days. Then, cells were stimu-
lated with IFN-g and were treated separately with each one
the candidate drugs. 48 hours later, immune CD45+ cells
and epithelial (EPCAM+) cells were identified via flow
cytometry and IFN-g dependent expression of PDL-1 and
IP-10 were measured via FACS and ELISA, respectively.

Drugs that affected human primary lung cells were further tested in-vivo in a mouse DTH model.

Mouse DTH in-vivo assay is an inflammatory model which is known as type IV hypersensitivity reactions and is mediated by soluble antigens primarily involving CD4+ or CD8+ T cell activation. This assay is characterized by the release of mediators from activated T cells. The T cells then activate local endothelial cells and recruit macrophages, which results in local inflammation and swelling. In this assay, female BALB/c mice were sensitized on the shaved abdominal skin with 100 μl of 2% oxazalone dissolved in acetone/olive oil [4:1 (vol/vol)] applied topically (day 0). DTH sensitivity was elicited 6 days later by challenging the mice with 20 μl of 0.5% oxazalone in acetone/olive oil, 10 μl administered topically to each side of the right ear. Control group was subcutaneously injected with Dexamethasone 100 μg/mouse in a total volume of 200 μl. 24 hr after challenge the swelling of the right ear was measured using a Micrometer, digital caliper (Mitutoyo Corp, Tokyo, Japan). The swelling of the left ear was served as control and the readout of this experiment model was the delta between the right and left ear (FIG. 15E).

Generally, drugs that showed a pro-inflammatory effect in this assay, are directed to treating or preventing graft versus host disease (GVHD), or cancer progression and can be further tested for their anti-tumor properties alone or with a combination with immunotherapy compound, whereas drugs that showed anti-inflammatory effect in this assay, are directed to treating or preventing an autoimmune disease or condition, inflammation, or viral infection.

Figure 15A:
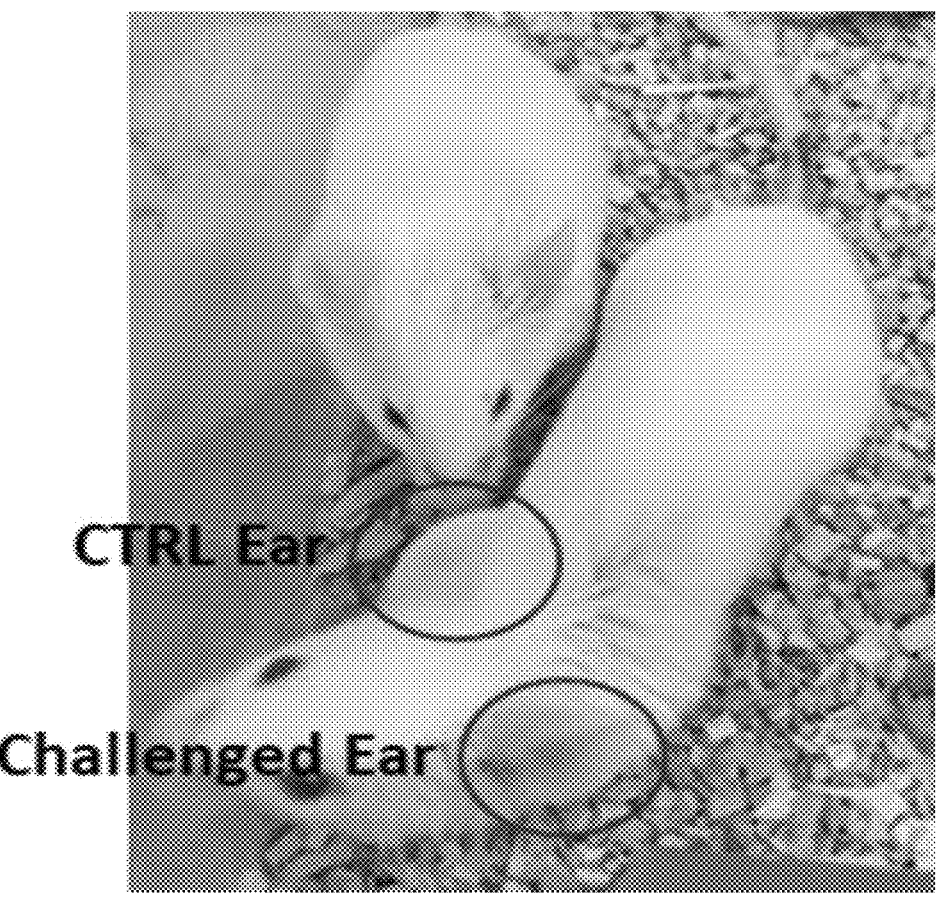
FIGS. 15A-15E include an image, micrographs, and a vertical bar graph showing a challenge experiment in a DTH murine model. (15A) a control Balb/c mice challenged in its right ear which is red and swollen.
Figures 15B, 15C, 15D:
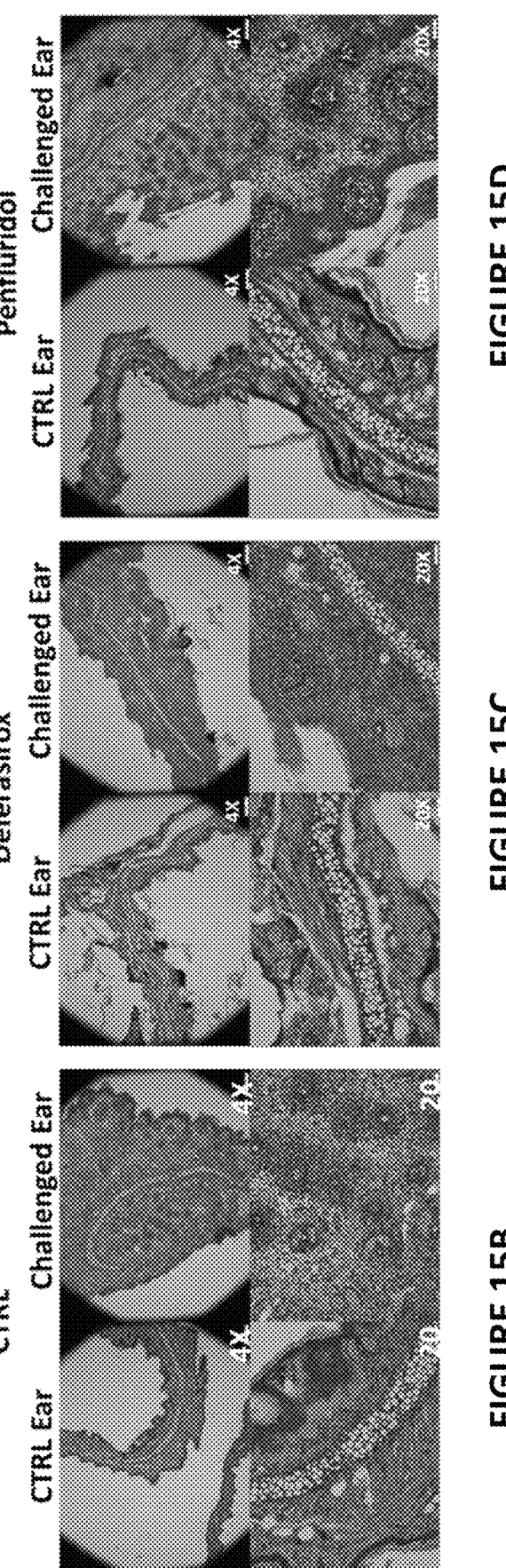
Figure 15E:
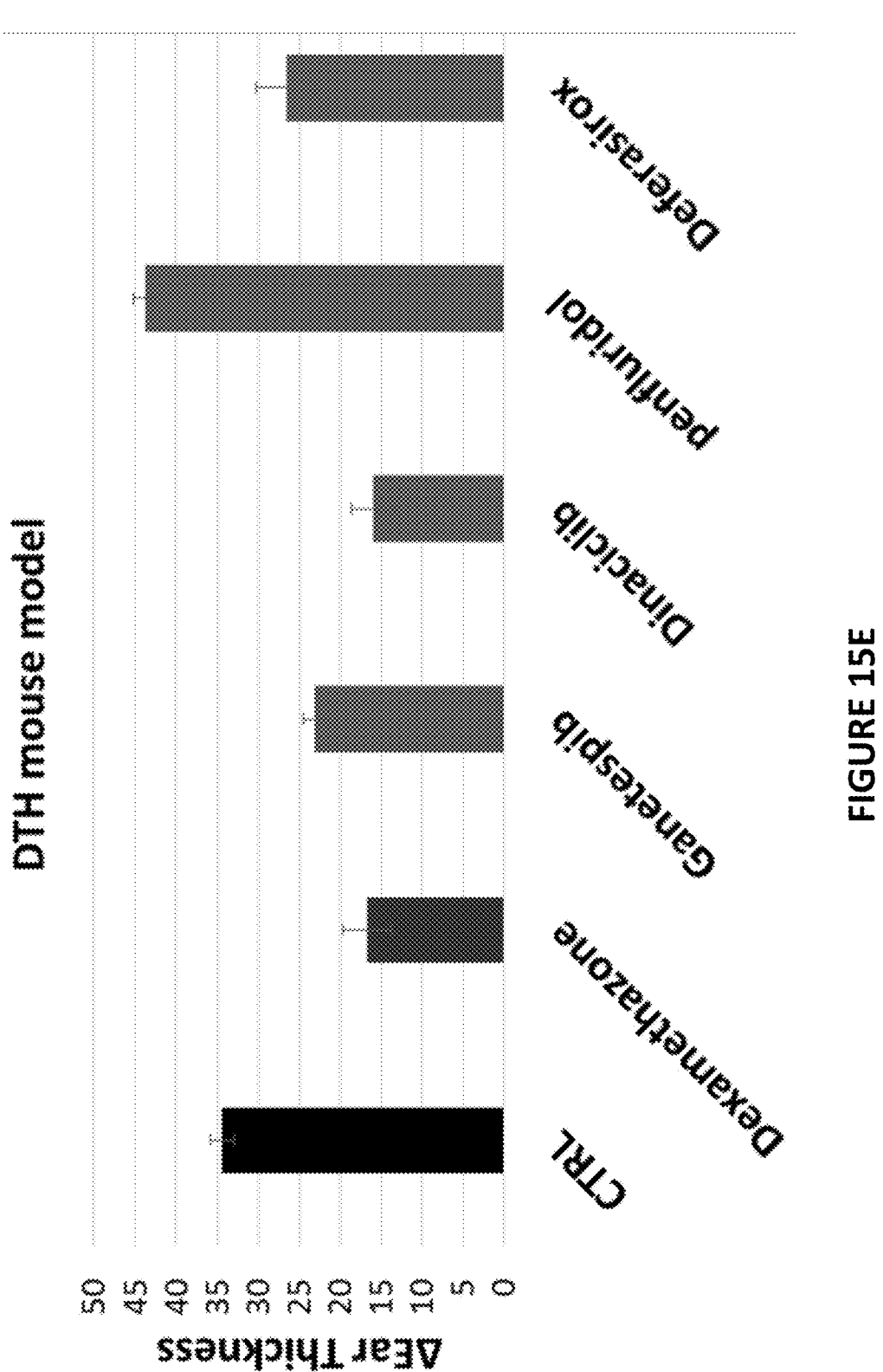
Figure 16A:
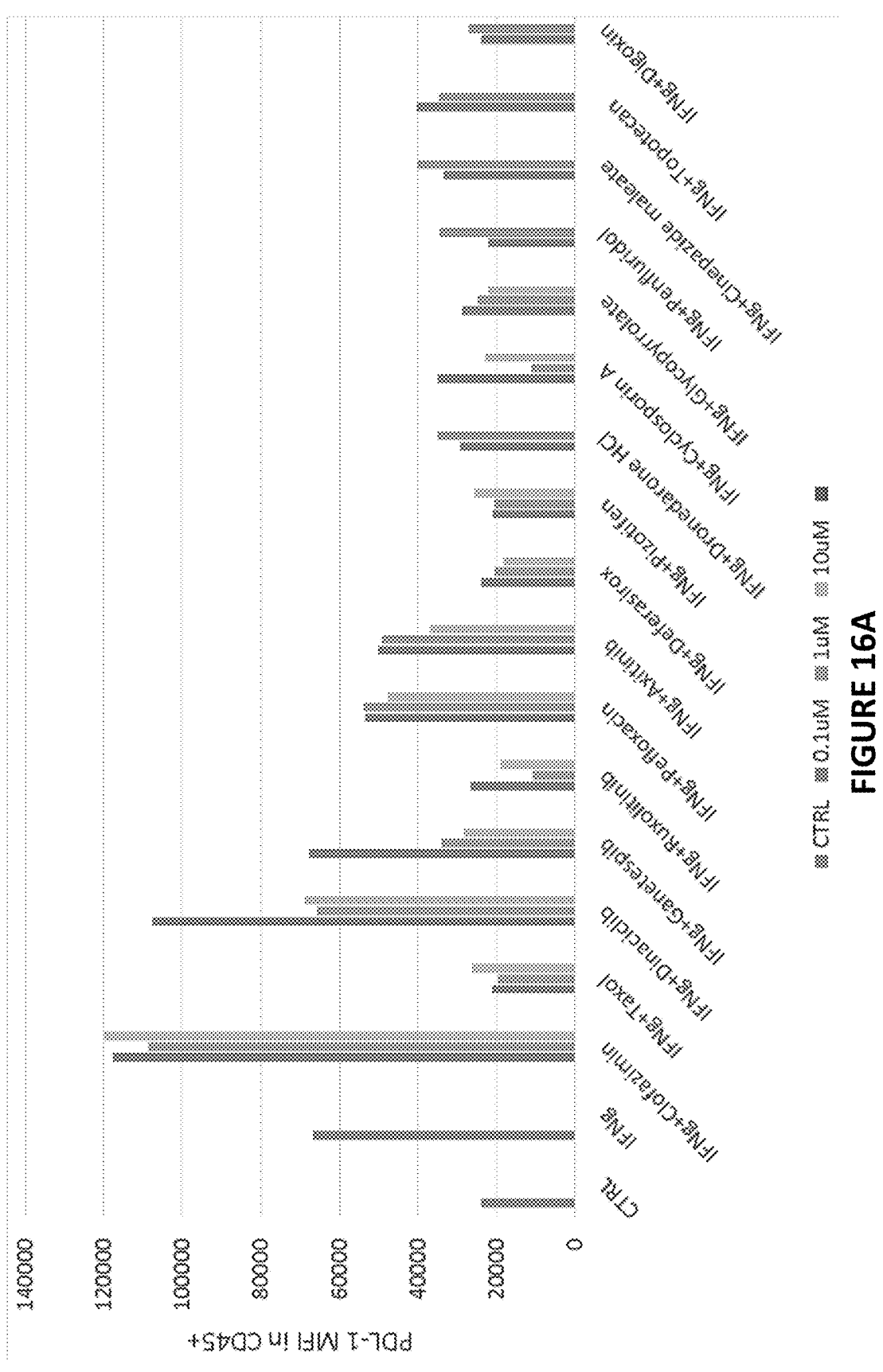
FIGS. 16A-16C include vertical bar graphs showing the effect of selected drugs on the expression of PDL-1 in human primary lung immune (CD45+; 16A) and epithelial (EPCAM+; 16B) cells, measured via flow cytometry, and the IP-10 levels in their supernatant's cell culture measured via ELISA (16C).
Figure 16B:
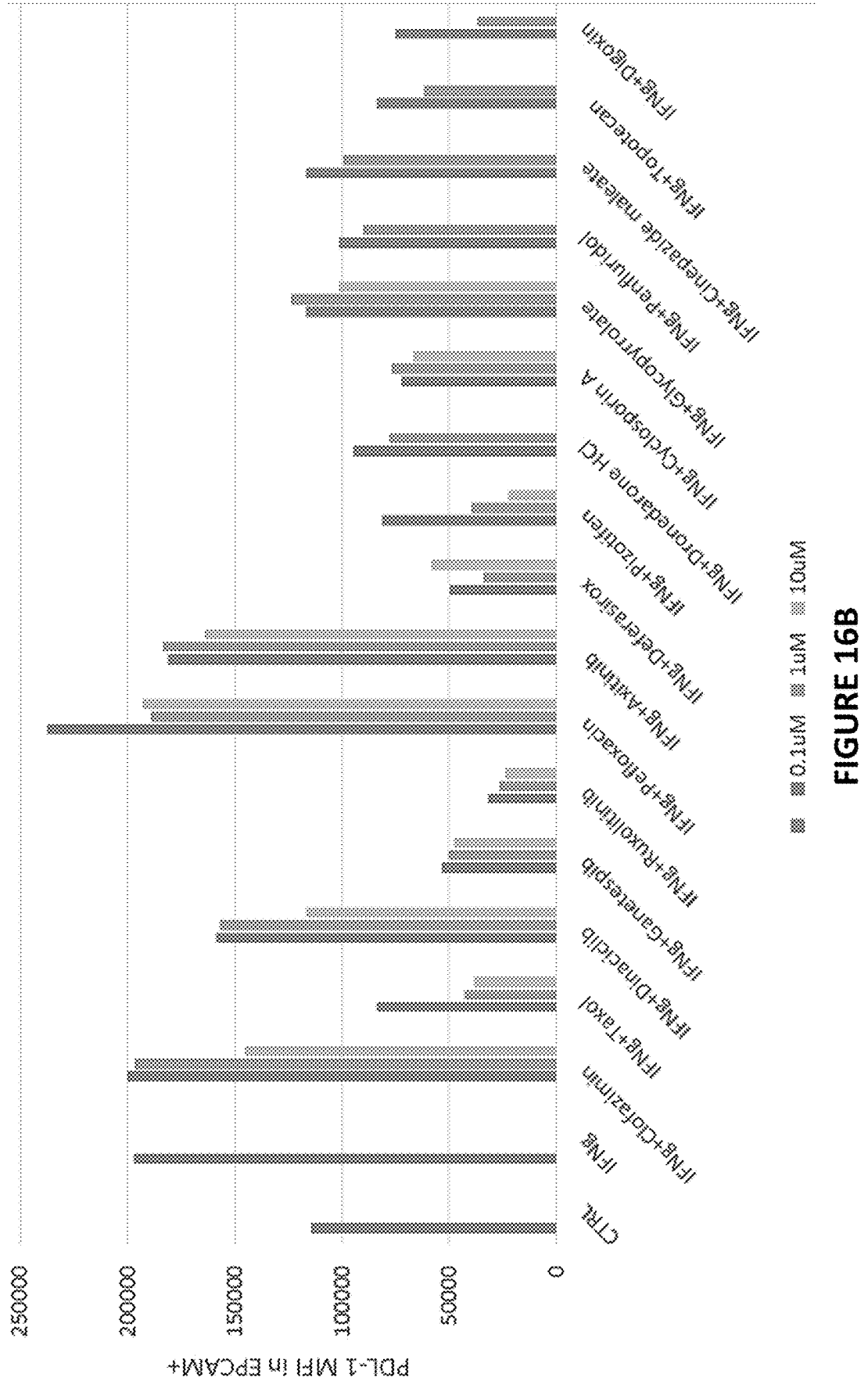
Figure 16C:
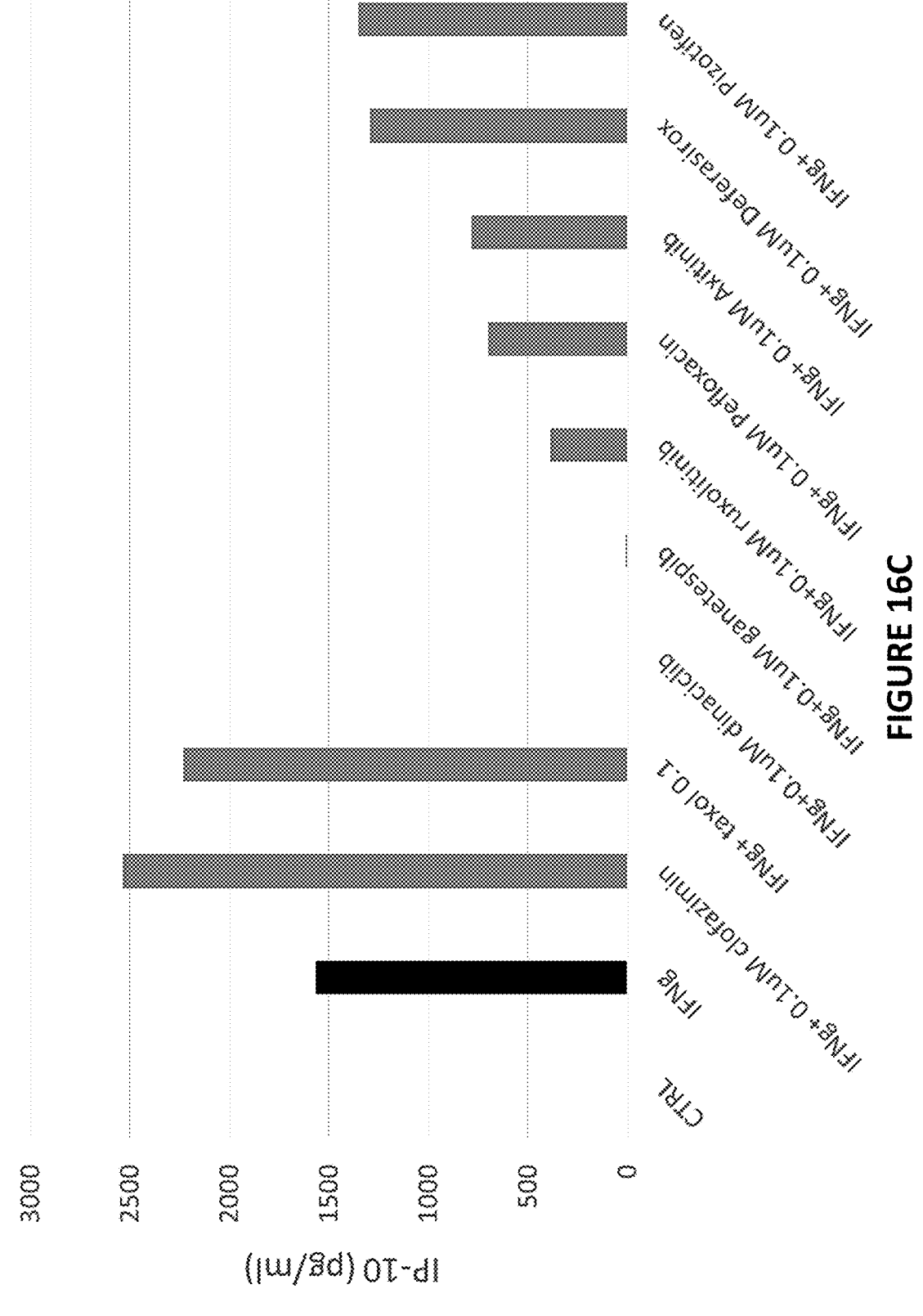

Specifically, Penfluridol had a pro-inflammatory effect in this model, while Deferasirox had an anti-inflammatory effect (FIGS. 15C-15D).

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A method for treating local inflammation in a subject in need thereof, the method comprising administering to the subject a pharmaceutical composition comprising a therapeutically effective amount of a Dinaciclib, thereby treating the local inflammation in the subject.

2. The method of claim 1, further comprising a step before said administering, comprising selecting a subject afflicted with said local inflammation.

3. The method of claim 1, wherein said administering comprises single administering or multiple administering.

4. The method of claim 1, wherein said administering comprises intravenously administering.

5. The method of claim 1, wherein said treating comprises inducing local anti-inflammatory effect comparable to steroid control.

6. The method of claim 5, wherein said steroid control comprises dexamethasone.

* * * * *